United States Patent
Henderson et al.

(10) Patent No.: US 8,257,431 B2
(45) Date of Patent: Sep. 4, 2012

(54) MULTI-FURCATED EPTFE GRAFTS AND STENT-GRAFT PROSTHESES AND METHODS OF MAKING THE SAME

(75) Inventors: Jamie Henderson, Oakland, NJ (US); Krzysztof Sowinski, Wallington, NJ (US); Ronald Rakos, Neshanic Station, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1183 days.

(21) Appl. No.: 11/591,303

(22) Filed: Nov. 1, 2006

(65) Prior Publication Data

US 2008/0103587 A1    May 1, 2008

(51) Int. Cl.
    *A61F 2/82* (2006.01)
(52) U.S. Cl. .......... 623/1.35; 623/1.13; 623/1.1
(58) Field of Classification Search ........... 623/1.35, 623/1.49, 1.1, 1.13; *A61F 2/82*
    See application file for complete search history.

(56) References Cited

U.S. PATENT DOCUMENTS

| | | | |
|---|---|---|---|
| 3,953,566 A | 4/1976 | Gore | |
| 3,962,153 A | 6/1976 | Gore | |
| 4,973,609 A | 11/1990 | Browne | |
| 4,994,071 A | 2/1991 | MacGregor | |
| 5,342,387 A | 8/1994 | Summers | |
| 2003/0114923 A1* | 6/2003 | Swanick et al. | 623/1.35 |
| 2005/0154442 A1 | 7/2005 | Eidenschink et al. | |

FOREIGN PATENT DOCUMENTS

| | | |
|---|---|---|
| WO | 98/33638 | 8/1998 |
| WO | 01/21107 A1 | 3/2001 |
| WO | 2005/120398 A1 | 12/2005 |

OTHER PUBLICATIONS

PCT Notification of Transmittal of the International Search Report and the Written Opinion of the International Searching Authority, or the Declaration for PCT/US2007/083327, mailed on Apr. 18, 2008 (1 page).
PCT International Search Report for PCT/US2007/083327, mailed on Apr. 18, 2008 (4 pages).
PCT Written Opinion of the International Searching Authority for PCT/US2007/083327, mailed on Apr. 18, 2008 (4 pages).

* cited by examiner

*Primary Examiner* — Thomas J Sweet
*Assistant Examiner* — Jason-Dennis Stewart
(74) *Attorney, Agent, or Firm* — Vidas, Arrett & Steinkraus, P.A.

(57) ABSTRACT

Methods of making multi-furcated grafts and, more particularly, a bifurcated graft from at least one ePTFE member are provided. Also provided are grafts made according to such methods.

20 Claims, 14 Drawing Sheets

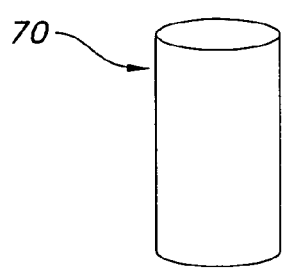
FIG. 4A
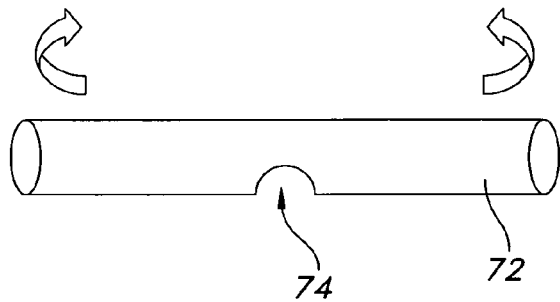
FIG. 4B
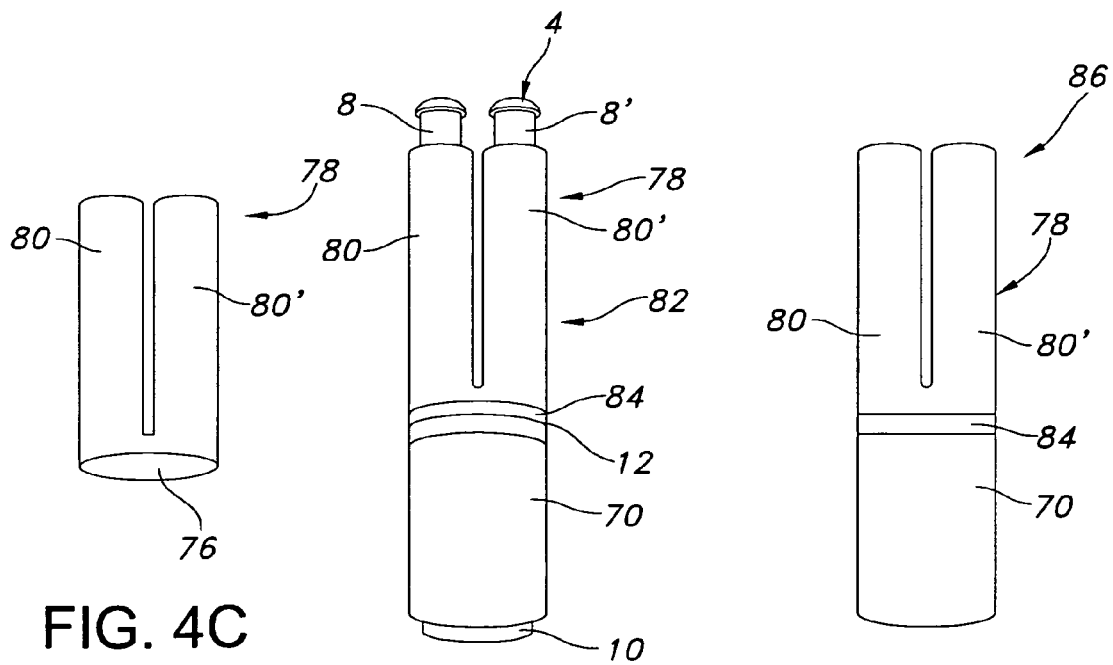
FIG. 4C
FIG. 4D
FIG. 4E

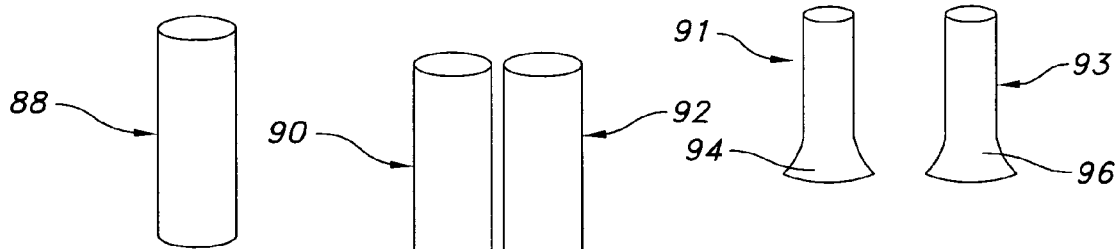
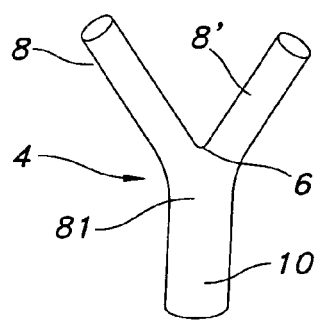
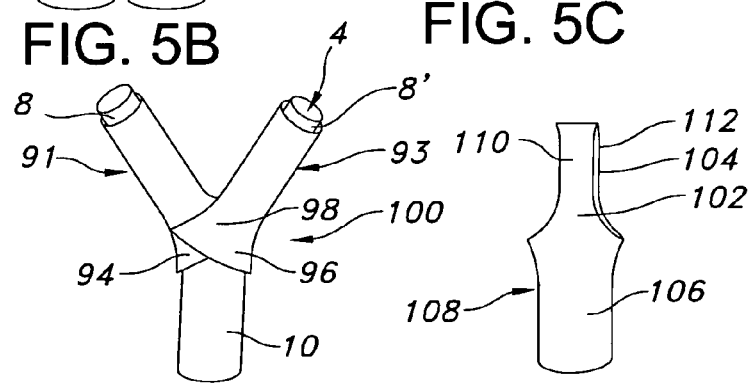
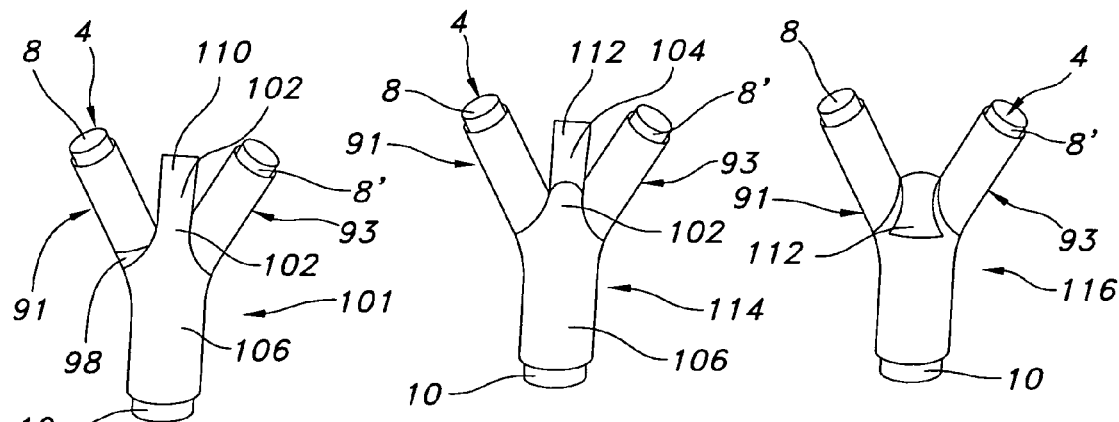
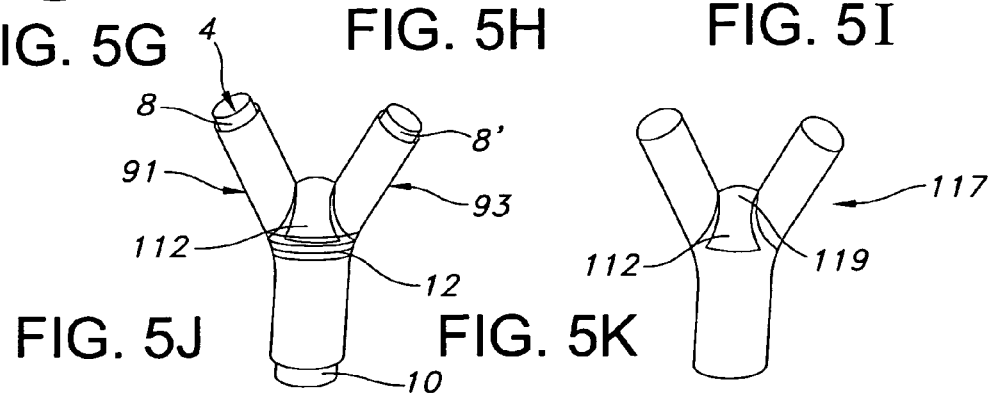

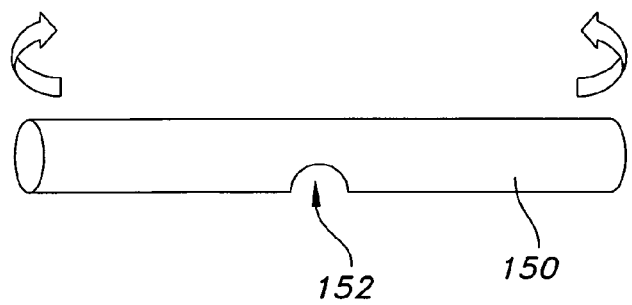
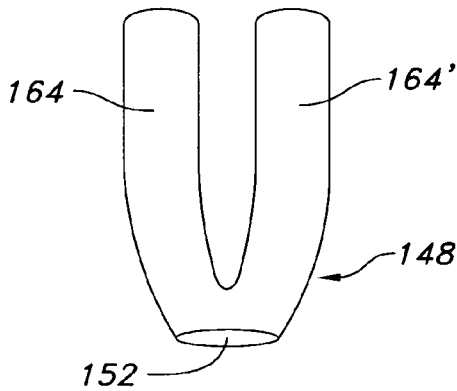
FIG. 7A    FIG. 7B
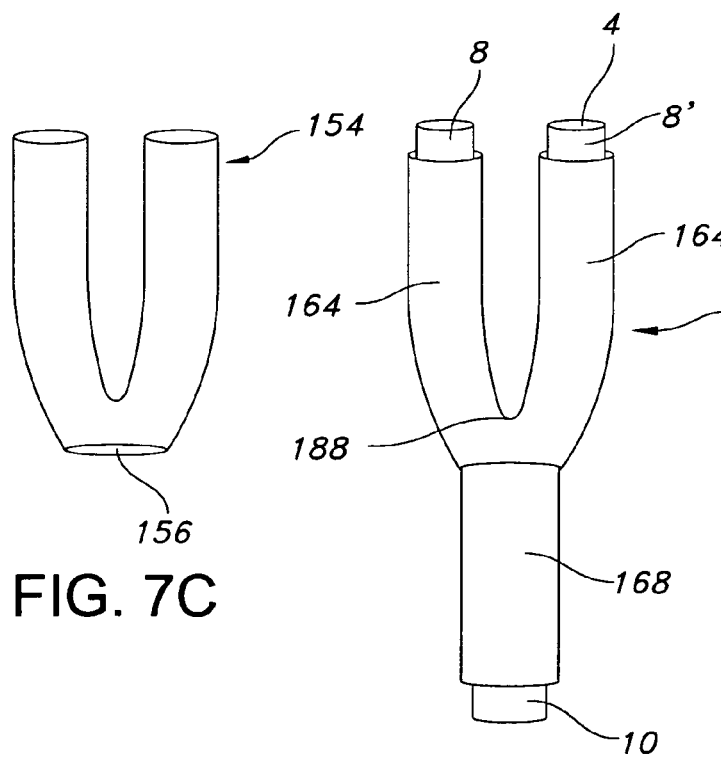
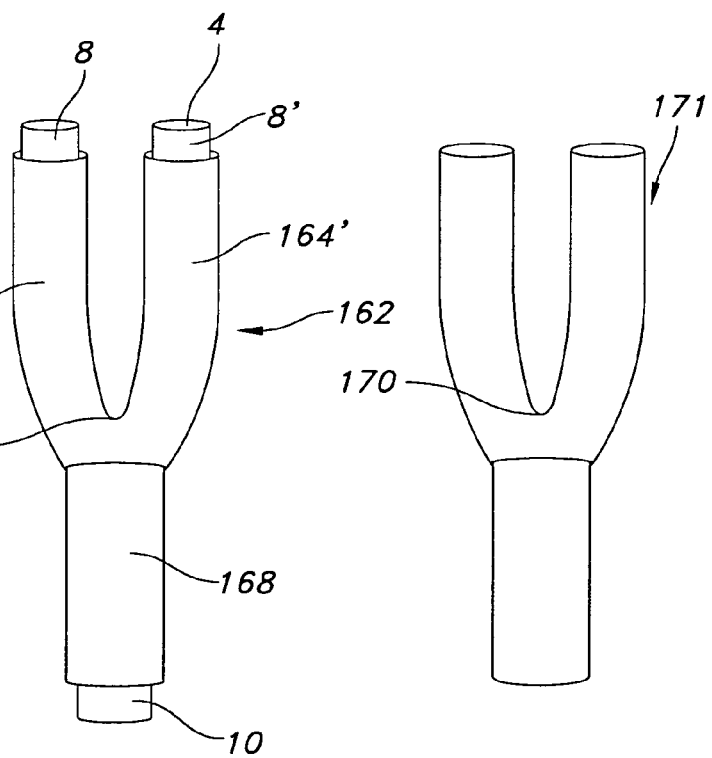
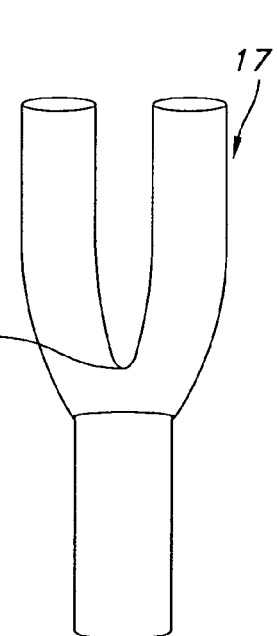
FIG. 7C    FIG. 7D    FIG. 7E

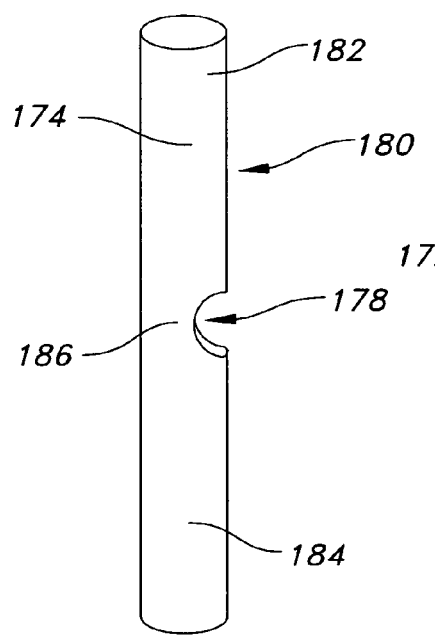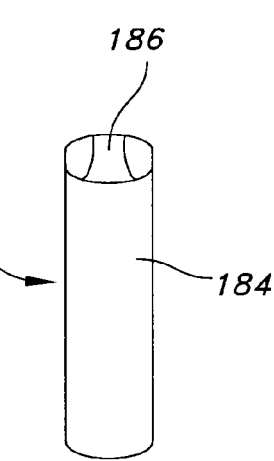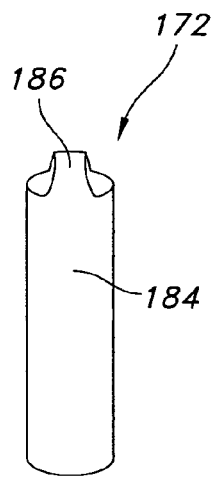
FIG. 8A  FIG. 8B  FIG. 8C
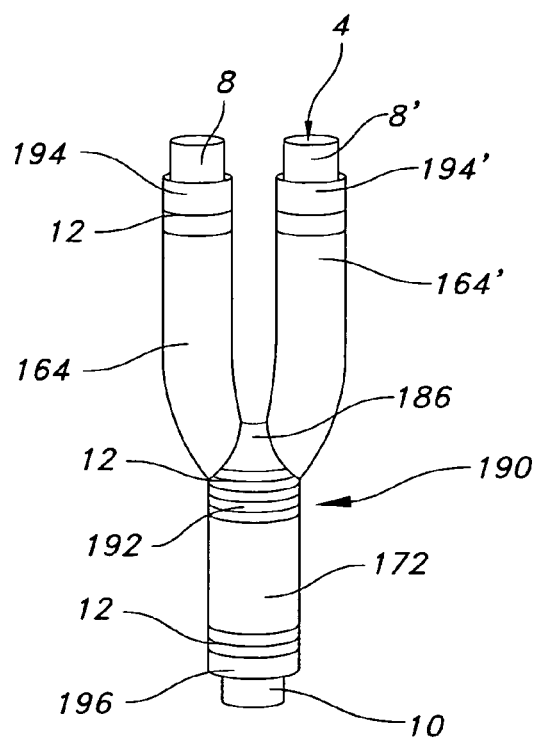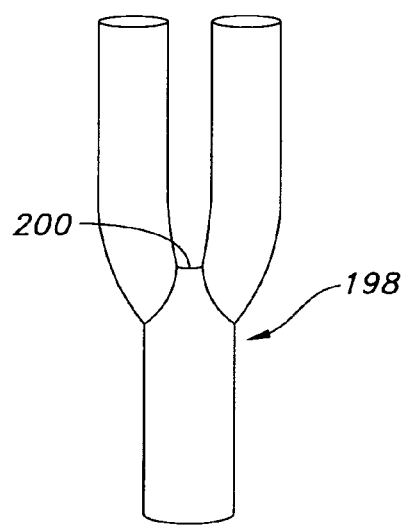
FIG. 8D  FIG. 8E

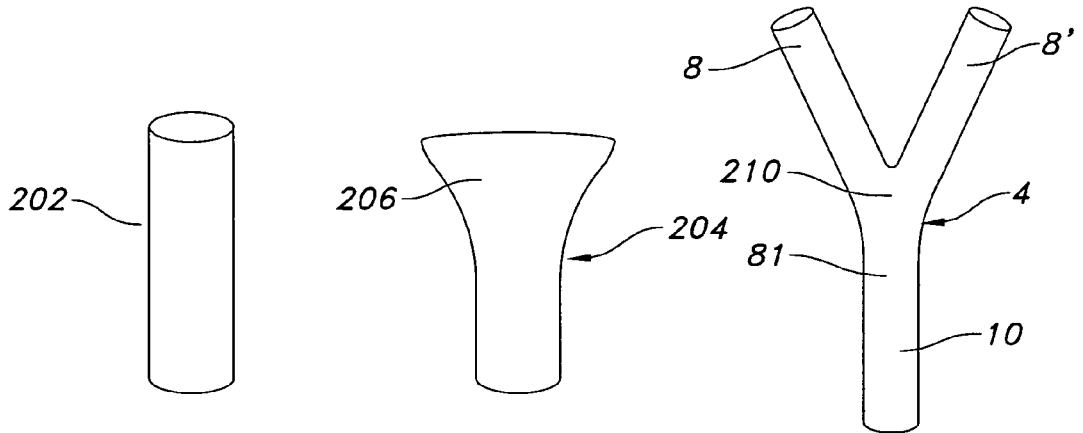
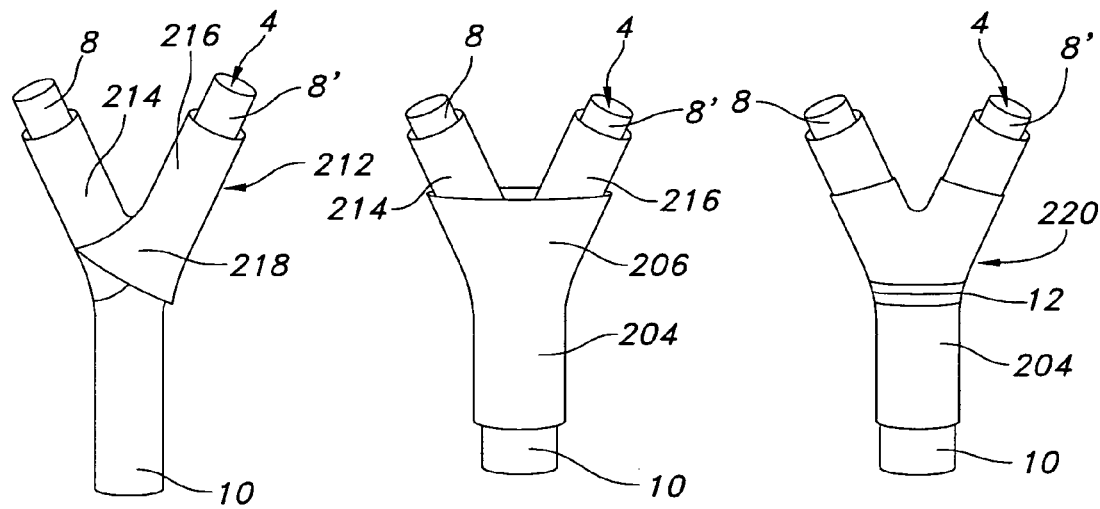
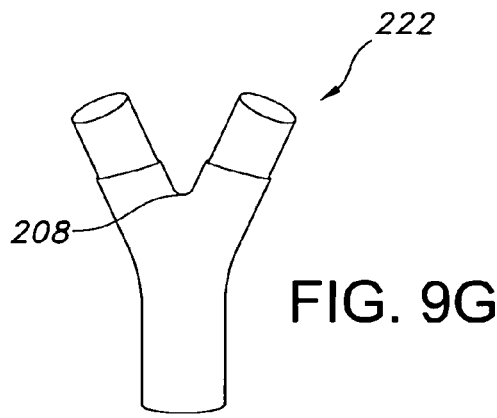

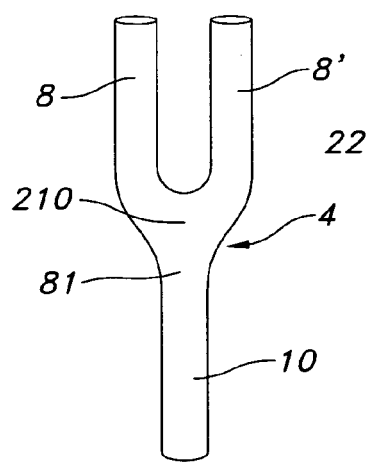 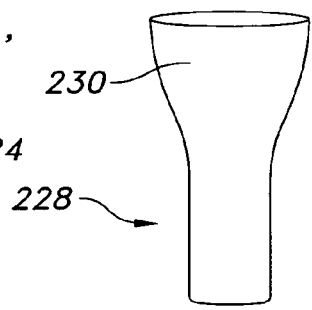 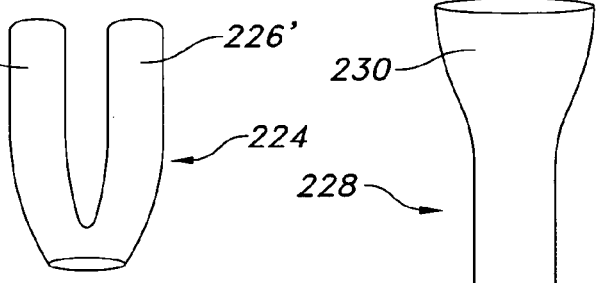
FIG. 10A   FIG. 10B   FIG. 10C
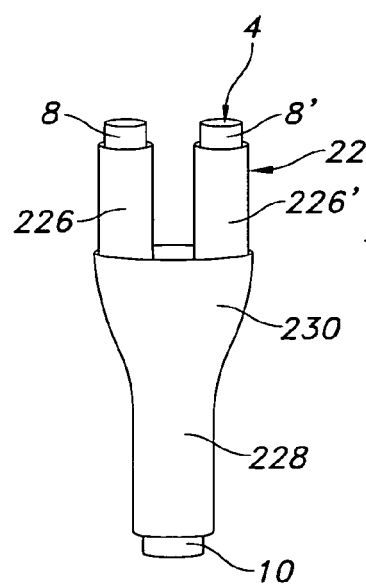 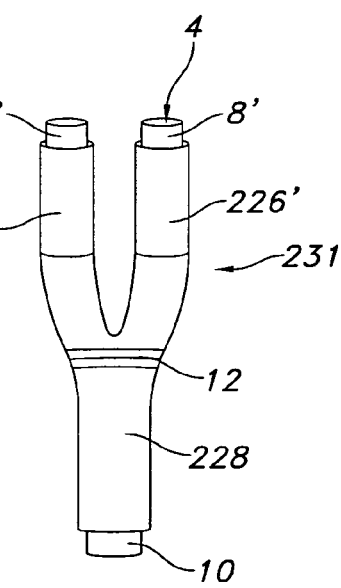 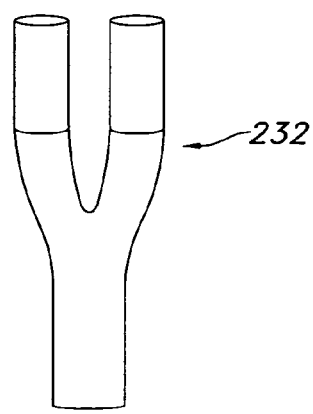
FIG. 10D   FIG. 10E   FIG. 10F

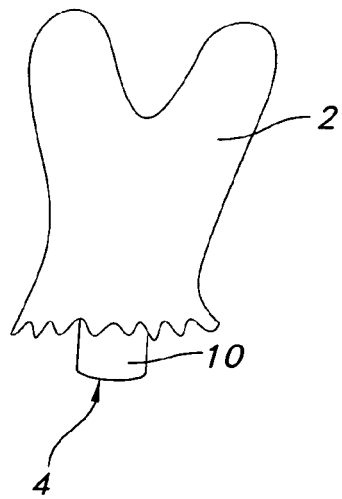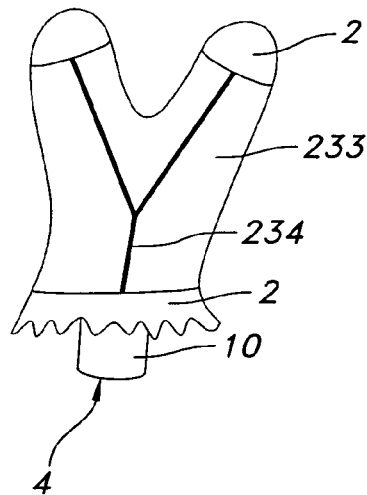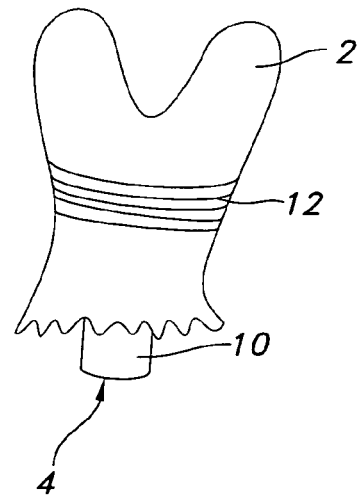
FIG. 11A   FIG. 11B   FIG. 11C
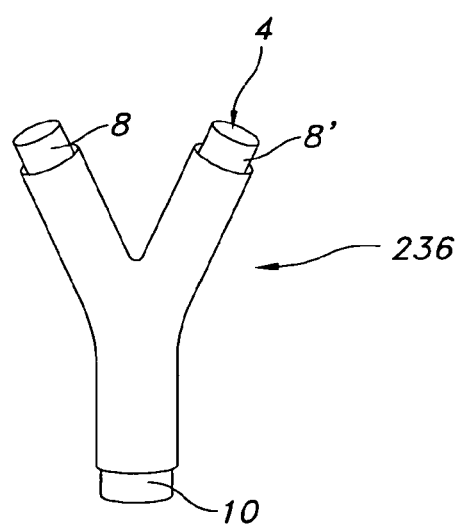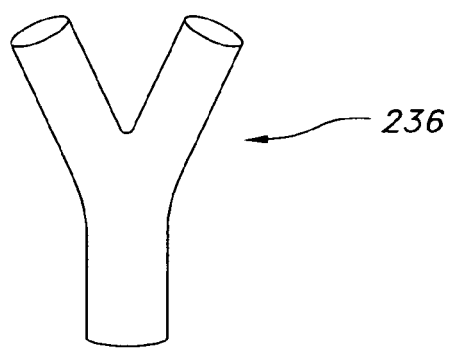
FIG. 11D   FIG. 11E

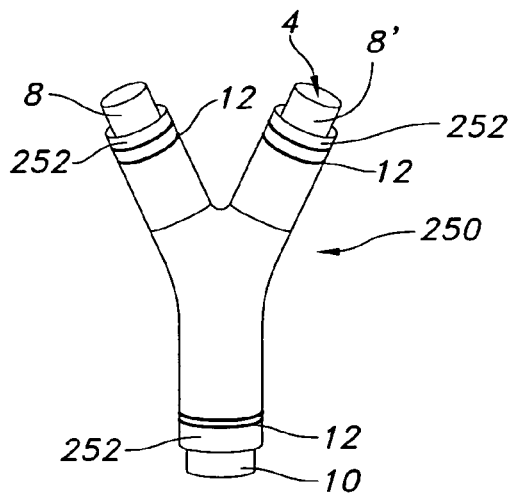
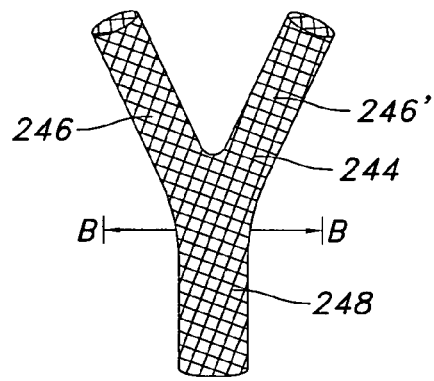
FIG. 12A
FIG. 12B
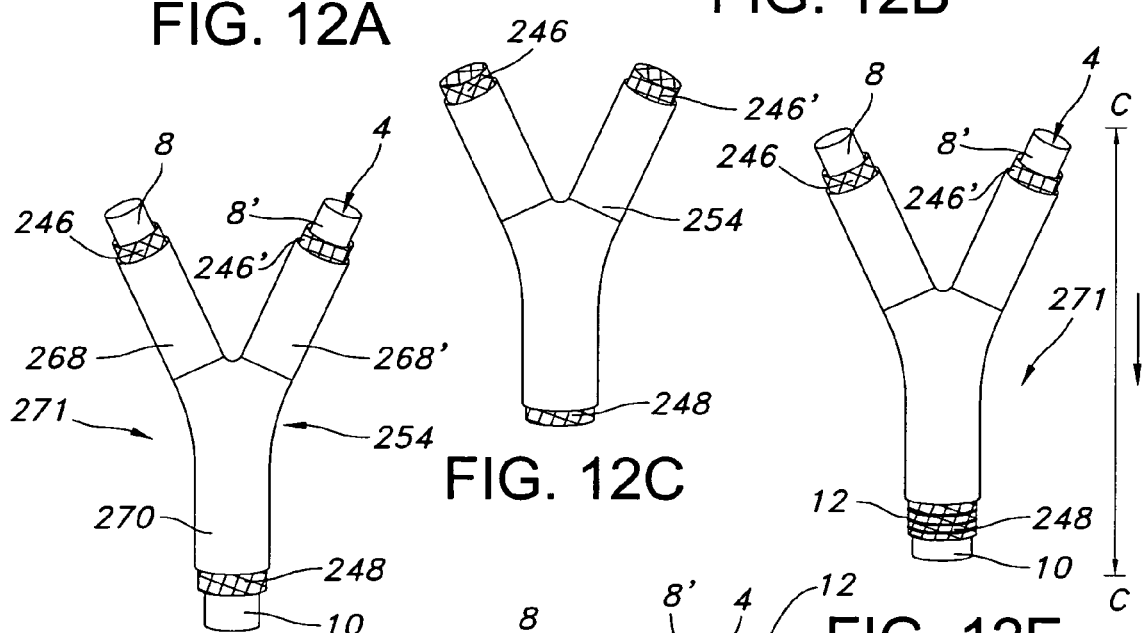
FIG. 12C
FIG. 12D
FIG. 12E
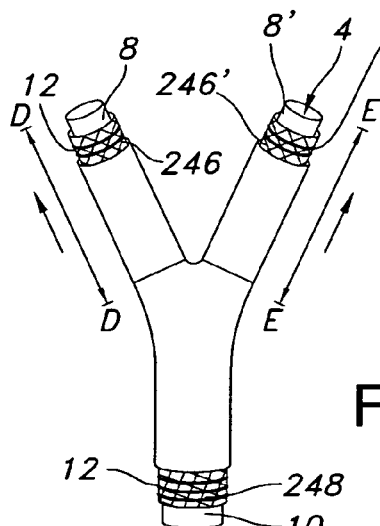
FIG. 12F
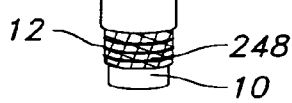

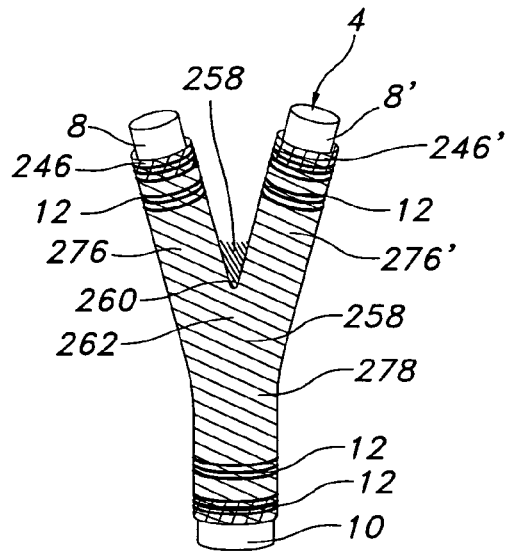
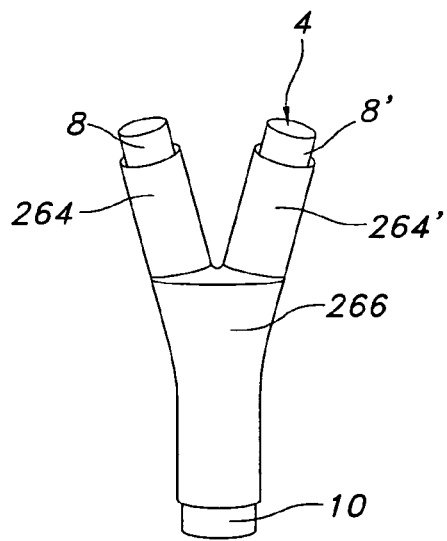
FIG. 12G
FIG. 12H
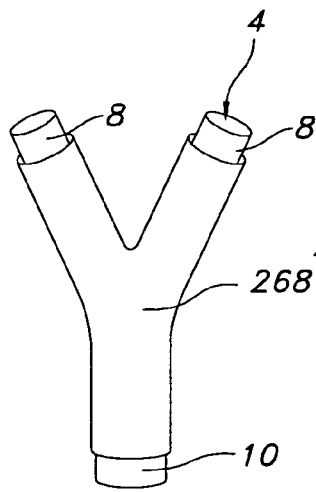
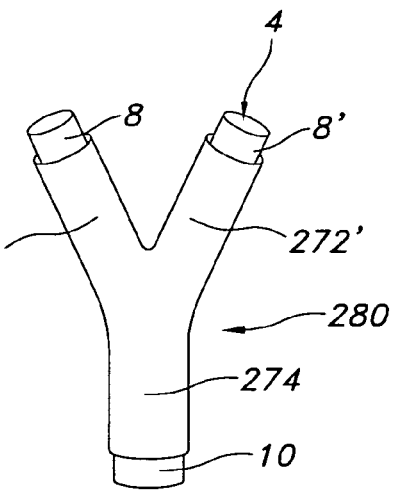
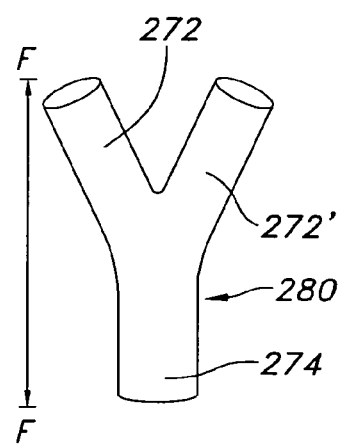
FIG. 12I
FIG. 12J
FIG. 12K

MULTI-FURCATED EPTFE GRAFTS AND STENT-GRAFT PROSTHESES AND METHODS OF MAKING THE SAME

FIELD OF THE INVENTION

The present invention relates generally to implantable prostheses. More particularly, the present invention relates to multi-furcated grafts and, more particularly, bifurcated grafts having at least one layer of expanded polytetrafluoroethylene (ePTFE), stent-grafts having at least one layer of ePTFE as a graft layer in combination with a stent layer, and methods of making the same.

BACKGROUND OF THE INVENTION

Implantable prostheses are commonly used in medical applications. One of the more common prosthetic structures is a tubular prosthesis which may be used as a vascular graft to replace or repair a damaged or diseased blood vessel. In particular, tubular prostheses such as vascular grafts are commonly used to repair or replace damaged or diseased vessels including damaged or diseased vessels occurring at non-uniform sites such as bifurcation points.

A bifurcation point is generally where a single lumen or artery (often called the trunk) splits into two lumens or arteries (often called branches) such as in a "Y" configuration. For example, one such bifurcation point is found within the human body at the location where the abdominal aortic artery branches into the left and right (or ipsalateral and contralateral) iliac arteries. Treatment of a bifurcation point afflicted with such defects as an occlusion, stenosis, or aneurysm is a particularly demanding application for grafts, stents or stent-grafts. Bifurcation points are exposed to high mechanical stresses based on the hemodynamics of flow at such sites. Specifically, high turbulence of blood flow is caused, for example, by the change in direction of flow as well as diminished vessel size beyond the bifurcation point. The bifurcation point of any graft or stent-graft must therefore be able to withstand high levels of mechanical stress.

It is well-known to form a tubular graft from polymers such as polytetrafluoroethylene (PTFE). Moreover, as is well-known, a tubular graft may be formed by stretching and expanding PTFE into a structure referred to as expanded polytetrafluoroethylene (ePTFE). Expanded PTFE consists of a unique microstructure of nodes interconnected by fibrils.

It is particularly desirable to make implantable prostheses from ePTFE as ePTFE exhibits many desirable characteristics. In particular, ePTFE exhibits the desirable characteristics of superior biocompatibility and low thrombogenicity. Moreover, tubes of ePTFE may be formed to be exceptionally thin yet exhibit the requisite strength necessary to serve in the repair or replacement of a body lumen. The thinness of ePTFE tubes facilitates ease of implantation and deployment with minimal adverse impact on the body.

Moreover, ePTFE in many ways satisfies a goal in graft technology to mimic, as closely as possible, the natural function of the blood vessel being replaced. Expanded PTFE is strong enough to resist tear and other mechanical damage under normal conditions, sufficiently flexible and compliant to accommodate the natural variability of blood flow and pressure, and sufficiently porous to allow for enhanced healing and appropriate tissue ingrowth when it is desired to anchor a prosthesis made therefrom within a blood vessel of the body.

Additionally, as the process of expanding PTFE into a cylindrical shape can result in a tubular graft having uniform or substantially uniform node and fibril size and orientation, tubular grafts made from ePTFE, as a general matter, are particularly strong due to the underlying uniformity of the ePTFE microstructure.

Attempts to form bifurcated or other complicated shaped structures by expanding PTFE into non-uniform or complicated shapes, however, have met with difficulties. For example, stretching and expanding PTFE into a Y-shaped, bifurcated graft is difficult and may result in non-uniform node and fibril size and orientation. A graft so formed may disadvantageously have properties which are not uniform throughout the graft as a result. Furthermore, when Y-shaped grafts are stretched, the nodes and fibrils of the least uniform size and orientation are likely to be predominantly located at the bifurcation point of the Y-shaped graft. These attributes make the non-uniform section (e.g., the bifurcation point) of the graft less strong than the more uniformly sized and oriented sections of the graft. As discussed above, however, it is the bifurcation point where high levels of mechanical stress can exist.

Methods for making bifurcated ePTFE grafts to date include forming multiple tubular sections of ePTFE and attaching them to one another to form a bifurcated graft. For example, it is possible to form a trunk and branches separately and then combine them to form an integral bifurcated graft. Such methods involve, for example, forming a seam at the juncture between the trunk and branch sections by lamination, co-melting, stitching or other attachment methods known in the art. Formation of such a seam at a bifurcation point may be disadvantageous because that section of the graft may see heightened mechanical stress when placed in the body.

Accordingly, there is a need for new methods of making a bifurcated implantable prosthesis which overcome the disadvantages of the prior art.

SUMMARY OF THE INVENTION

In one aspect of the invention, there is provided a method of making a graft. The method includes the steps of: (i) providing at least one PTFE member; and (ii) placing the PTFE member onto a mandrel having a trunk and at least two branches, wherein the branches define at least one crotch area, and wherein a continuous, uninterrupted section of the PTFE member spans the crotch area of the mandrel.

In another aspect of the invention, there is provided a graft including: (i) a trunk; (ii) at least two branches; and (iii) at least one PTFE member, wherein the branches define at least one crotch area, and wherein a continuous, uninterrupted section of the PTFE member spans at least a portion of the crotch area.

BRIEF DESCRIPTION OF THE DRAWINGS

FIGS. 4A to 4E illustrate an embodiment of the subject invention wherein a bifurcated graft is formed from two tubular ePTFE members.

FIGS. 5A to 5K illustrate an embodiment of the subject invention wherein a bifurcated graft is formed from three tubular ePTFE members.

FIGS. 7A to 7E illustrate an embodiment of the subject invention wherein a two-layered bifurcated graft is formed.

FIGS. 8A to 8E illustrate an embodiment of the subject invention wherein a four-layered bifurcated graft form is formed.

FIGS. 9A to 9G and 10A to 10F illustrate additional embodiments of the subject invention wherein bifurcated grafts are formed from shaped ePTFE forms.

FIGS. 11A to 11E illustrate an embodiment of the subject invention wherein a three-layered bifurcated graft having a seamless inner ePTFE layer and a seamless outer ePTFE layer is formed.

FIGS. 12A to 12K illustrate an embodiment of the subject invention wherein a bifurcated stent-graft is formed by means of lamination with silicone.

DETAILED DESCRIPTION OF THE INVENTION

Figure 1A:
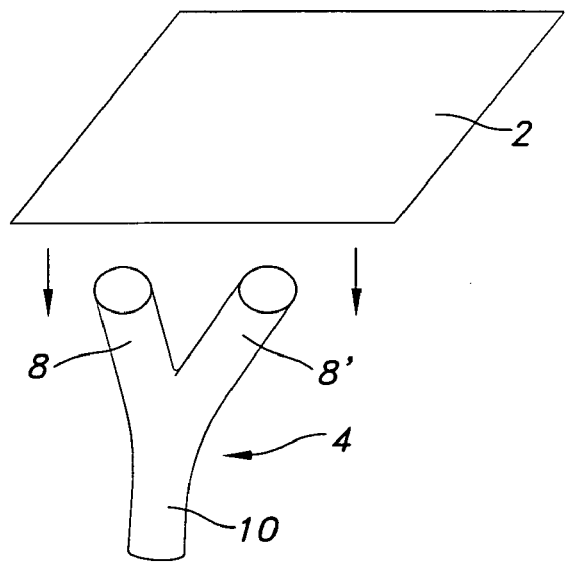
FIGS. 1A to 1D and 2A to 2K illustrate an embodiment of the subject invention wherein a bifurcated graft is formed from a single sheet of ePTFE.

In one aspect of the invention, there is provided multi-lumen or multi-furcated ePTFE grafts and methods of making such ePTFE grafts such that their uniformity in node and fibril structure, and subsequent physical and mechanical properties can be tailored. The present invention further provides for multi-furcated grafts which have one or more crotch sections formed from one or more continuous ePTFE sections which are desirably free from welds, laminations or other common ePTFE joining techniques.

In another aspect of the invention, a bifurcated graft is disclosed wherein at least one continuous, uninterrupted section of ePTFE spans the bifurcation point. Desirably, the ePTFE spanning the bifurcation point possesses a uniform node and fibril structure or a substantially uniform node and fibril structure. Moreover, the ePTFE at the bifurcation point is desirably free of any weld, sintered seam, adhered portion, laminated portion or sewn portion. The bifurcated graft may have a reinforced bifurcation point that is covered by multiple layers of a continuous, uninterrupted section of ePTFE.

The term "furcated" refers to grafts having one or more branches or lumens off of a lumen. A multi-furcated graft refers to grafts with multiple branches.

The term "bifurcation point," as used herein, refers to the point or area in a graft or stent-graft of the subject invention in which the graft or stent-graft divides into two branches and which retains a trunk portion.

The term "crotch," as used herein, refers to the transitional section of a graft or stent-graft where the graft or stent-graft transitions from the branches of a multi-furcated graft to the trunk. The term, as used herein, includes the bifurcation point of the graft or stent-graft.

The term "stomach," as used herein, refers to the section of the trunk of a multi-furcated graft or stent-graft that is between the waist section and base of the trunk.

The term "waist," as used herein, refers to the section of the trunk of a multi-furcated graft or stent-graft that is between the crotch section and the stomach section of the graft or stent-graft.

The term "proximal," when used in connection with a graft or stent-graft, refers to being downstream with respect to the direction of blood flow.

The term "distal," when used in connection with a graft or stent-graft, refers to being upstream with respect to the direction of blood flow.

It is understood that those aspects of the invention which are recited with respect to bifurcated grafts, including the applicable defined terms, are also applicable to grafts having more than two branches, such as tri-furcated grafts, and the invention is intended to include all such embodiments.

PTFE and ePTFE Materials and Formation of the Same

The grafts and stent-grafts of the subject invention can be formed using any suitable PTFE member. In particular, the grafts of the subject invention can be formed using any suitable shaped form made of polytetrafluoroethylene (PTFE). Desirably, the shaped forms are made of expanded polytetrafluoroethylene (ePTFE). In particular, the shaped forms are desirably made from sheets and/or tubular members of ePTFE.

The sheets and tubular members of ePTFE can have any suitable thickness. Desirably, the ePTFE has a thickness from about 0.010 mm to about 1 mm. More desirably, the ePTFE has a thickness from about 0.050 mm to about 0.300 mm.

Moreover, the ePTFE of the subject invention can have any suitable porosity and intermodal distance (IND). Desirably, the IND may range from about one (1) micron to about one hundred and fifty (150) microns, and more desirably from about five (5) to about eighty (80) microns and even more desirably from about twenty (20) to about sixty (60) microns.

An ePTFE member for use in the subject invention can be manufactured using any suitable method known in the art. In particular, an ePTFE tubular or sheet member can be made from PTFE using any suitable method known in the art. One method for manufacturing porous PTFE tubing, is described, for example, in U.S. Pat. No. 3,953,566, U.S. Pat. No. 3,962,153, and U.S. Pat. No. 4,973,609, the entireties of which are herein incorporated by reference.

In particular, an ePTFE member can be made from a PTFE resin paste. For example, a fine, virgin PTFE powder such as F-104, F-103, Virgin PTFE Fine Powder (Dakin America, Orangeburg, N.Y.) can be admixed with a liquid lubricant such as odorless mineral spirits or naphtha, i.e., Isopar® (Exxon Chemical Co., Houston, Tex.), to form a PTFE resin paste of the desired consistency.

For tubular members, the PTFE resin paste is desirably passed through a tubular extrusion dye and dried. For sheets, the PTFE resin paste is provided on a flat substrate and the wet extrudate is dried at room temperature or near the lubricant's drying point to evaporate the lubricant.

The PTFE material so formed is referred to as a "green" extrudate or an unsintered extrudate. The "green" PTFE extrudate may be stretched and/or expanded to form ePTFE.

Expansion refers to increasing the presence of internal voids within the structure, as embodied in the creation of a node and fibril structure. Desirably, expansion occurs at a temperature less than about 315° C. More desirably, expansion occurs at a temperature from about 150° C. to about 300° C. using any suitable expansion rate. Both high expanded rate ePTFE and low expanded rate ePTFE are thus suitable for use in the subject invention. The ePTFE so formed is desirably sintered by heating it to a temperature from about 326° C. to about 400° C. This process results in an amorphous locking of the polymer.

Desirably, the ePTFE is uniaxially stretched. However, biaxially stretched ePTFE and multiaxially stretched ePTFE also are useful.

Characteristics of the Grafts of the Subject Invention

As further described in detail below, formation of a graft according to the present invention is accomplished by conforming one or more ePTFE tubular members to part or all of a mandrel. The shape and size of the mandrel is selected so as to approximate, as closely as practicable, the shape and size of the graft to be formed thereon. Accordingly, a bifurcated Y-shaped mandrel should be used when it is desired to form a bifurcated Y-shaped graft. Numerous other shapes are contemplated and are intended to be within the scope of the current invention.

The grafts, as described in detail below, may be grafts in which the various branches may be the same or different in length and/or diameter. The combined diameter of the branches may be generally about the same as, or slightly less than, the diameter of the trunk from which they emanate. For example, each branch, when approximately equivalent in diameter, desirably may have a diameter which is approximately half the diameter of the trunk. Additionally, the mandrel may be sized so that a graft formed thereon may be removed from the mandrel by pulling the main trunk portion of the graft over the branches of the mandrel. Desirably, the branches of the mandrel are substantially parallel to one another and are separated by a distance sufficient to permit ease of removal of the graft from the mandrel.

In certain embodiments, the grafts of the subject invention possess no overlapping sections or sealed portions. However, in other embodiments of the invention, overlapping sections of a graft will be treated so as to form a leak-free closure or seal. There are no particular limitations to the manner in which the seal is made. Exemplary methods include, for example, welding, sintering, bonding by means of adhesion (for example, with polyurethane-based materials such as Corethane® or fluorocarbon-based materials such as fluoroethylene polymers, laminating, stitching or otherwise sewing. Desirably, a seal so formed is not present at the crotch section, including the bifurcation point, of the grafts of the subject invention. Where an adhesive is used, a particularly useful fluoroethylene polymer is fluorinated ethylene propylene (FEP).

Grafts formed according to the present invention may be used alone or in combination with other embodiments shown herein. Any and all combinations that are possible are envisioned within the scope of the invention. Some desirable combinations are described in further detail below.

Formation of Grafts from ePTFE Sheets

In one aspect of the invention, multi- or bifurcated grafts are formed from one or more sheets of ePTFE. Desirably, planar and rectilinear sheets of ePTFE are used. Initially, the sheet may be unsintered, partially sintered or completely sintered.

Partial sintering involves heating the ePTFE at a temperature and for a time which will partially lock the internal polymeric structure of the ePTFE. For partial or complete sintering, heat-treating the ePTFE at a temperature of from about 337° C. to about 398° C. for from about 30 seconds to about 20 minutes is acceptable. Desirably, sintering will be performed at a temperature of from about 343° C. to about 354° C. for from about 2 minutes to about 10 minutes. One having skill in the art will be able to determine appropriate temperature and time ranges for the desired level of sintering for the particular ePTFE sheet being so treated.

Referring to the drawings, like characters refer to like parts throughout the several views. Moreover, the term bifurcation point as used in the figures should be understood as being synonymous with the term crotch.

Referring to FIGS. 1A to 1D, those figures show an embodiment of the present invention wherein a bifurcated graft in accordance with the subject invention is formed from a single sheet of ePTFE.

Figure 1B:
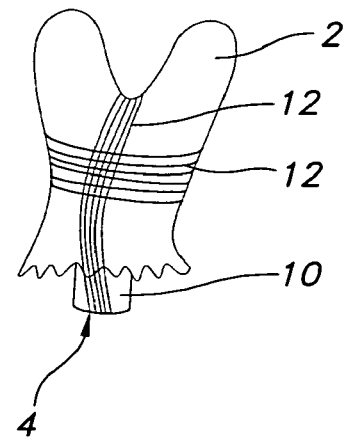

As shown in the perspective view in FIG. 1A, a sheet 2 of ePTFE is pulled over the top of a mandrel 4 in the direction shown by the arrows until the sheet 2 of ePTFE loosely surrounds the branches 8 and 8' and trunk 10 of mandrel 4 as shown in the perspective view in FIG. 1B.

Next, tape 12, such as Teflon™ tape, may be wrapped along a longitudinal axis defined by the trunk 10 of mandrel 4, and between the branches 8 and 8' of the mandrel 4, to secure the sheet 2 of ePTFE to the mandrel 4, as further shown in FIG. 1B. Additional tape 12 then may be wrapped around the circumference of the trunk 10 of the mandrel 4 to secure further the sheet 2 of ePTFE to mandrel 4, as also shown in FIG. 1B.

The sheet 2 of ePTFE then is heat-treated to heat-shrink the sheet 2 of ePTFE to the mandrel 4. In particular, heat-treating may be performed to sinter the ePTFE, either partially or completely. Desirably, the heat-treating step is performed so that the ePTFE is completely sintered. Suitable temperature ranges for this step are from about 346° C. to about 354° C. Desirably, the heat-treating step is performed at about 352° C. for about 5 minutes to about 30 minutes and more desirably from about 10 minutes to about 20 minutes.

Figure 1C:
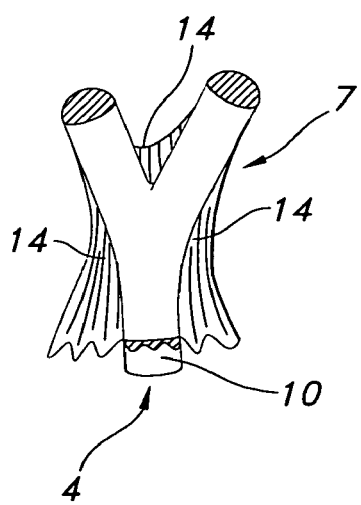
Figure 1D:
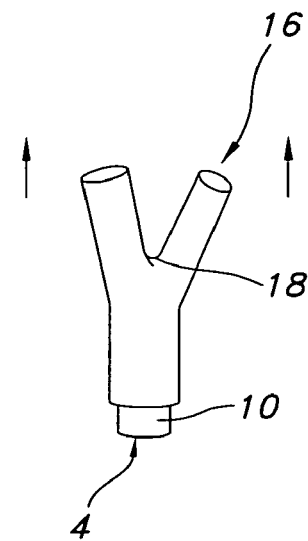

After heat-treating, the tape 12 is removed to form the intermediate graft product 7 shown in perspective view in FIG. 1C. As shown in FIG. 1C, the intermediate graft product 7 may have excess ePTFE 14 about the branches 8 and 8' and/or trunk 10 of the mandrel 4. Such excess ePTFE 14 about the branches 8 and 8' and/or trunk 10 of the mandrel 4 then is removed by any suitable means (such as cutting) to form the graft end product 16, which is shown in perspective view in FIG. 1D on mandrel 4. Thereafter, the graft end product 16 is removed from the mandrel 4 by pulling the same off of the mandrel 4 in a direction distal to the trunk 10 of the mandrel 4 in the direction shown by the arrows in FIG. 1D. A continuous, uninterrupted section of ePTFE spans the bifurcation point 18 of the graft end product 16 shown in FIG. 1D.

Figure 2A:
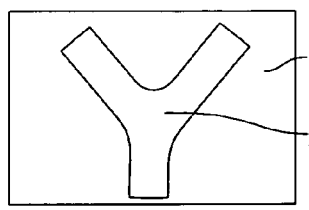

Referring to FIGS. 2A to 2K, another method for forming a bifurcated graft from a sheet 2 of ePTFE is shown. In accordance with a method of the subject invention, a Y-shaped mandrel (not shown) is impressed into a sheet 2 of ePTFE to form an impression 20 therein as shown in FIG. 2A, which is a top view of a sheet 2 of ePTFE with impression 20 formed therein. As shown in the top view in FIG. 2B, after the impression 20 is made, the sheet 2 of ePTFE is cut about the impression 20 into a shaped form 22 that can be completely impressed about a mandrel 4. As is apparent from FIG. 2B, the shaped form 22 has excess material 24 for wrapping about a mandrel 4 having two branches 8 and 8', a trunk 10, and a bifurcation point 6.

In some embodiments, sheets used to cover or wrap around a multi-furcated mandrel may be pre-formed into a shape which facilitates wrapping. For example, sheets may be pre-formed or pre-shaped using thermoforming techniques, molds, dies, vacuum-forming equipment or other means of pre-shaping for this purpose. In this manner, pre-shaped sheets may be formed to more completely cover the multi-furcated mandrel. In some embodiments, two pre-forms may be mated on opposite side of the mandrel to enclose the mandrel in a clam-shell configuration.

Figure 2B:
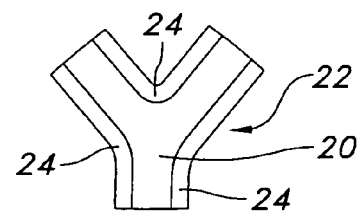
Figure 2C:
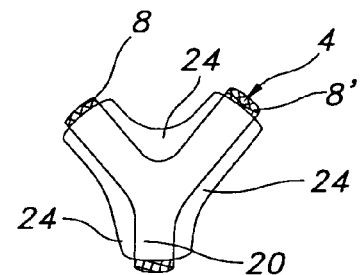
Figure 2D:
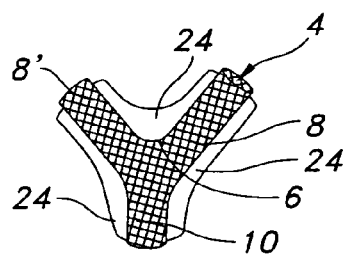
Figure 2E:
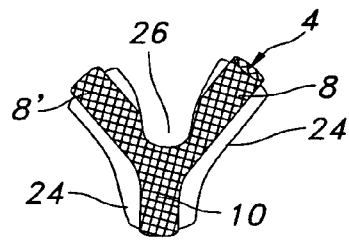

The shaped form 24 shown in FIG. 2B is then fitted onto one side of corresponding mandrel 4 as shown in the perspective view in FIG. 2C such that a continuous, uninterrupted section of ePTFE spans the bifurcation point of the mandrel. In particular, the impression 20 should substantially cover the one side and desirably the front side of the mandrel 4 as shown in FIG. 2C. Viewing the mandrel 4 of FIG. 2C from the opposing or back side as shown in FIG. 2D, excess material 24 between the branches 8 and 8' of the mandrel 4 is folded down such that a flap 26 is formed that covers the bifurcation point 6 on the back side of the mandrel 4 as shown in FIG. 2E. The remaining excess material 24 is then completely wrapped about the mandrel 4 such that seam 28, as shown in the perspective view in FIG. 2F, is formed on the back side of the mandrel 4 where the ePTFE overlaps as a result of the complete wrap-around.

Seam 28 then is treated to form a liquid-tight seal using any conventional method known in the art. For example, an adhesive may be placed between the overlapping sections and cured according to methods known in the art. Suitable adhesives for this purpose include fluoropolymers that melt at temperatures lower than that of ePTFE. Examples include, but are not limited to, fluoroethylene polymers (FEP), Corethane®, or styrene-isobutadiene-styrene copolymers (SIBS), which are commercially available. Desirably, the adhesive is FEP. Additionally, or in the alternative, heat and/or sintering with pressure may be used. When heating is used, excess ePTFE may be removed after heating.

Figure 2F:
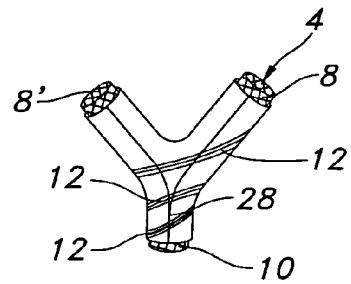

Additionally, or in the alternative, tape 12, such as Teflon™ tape, will be helically wrapped around the mandrel 4 that is wrapped with ePTFE as further shown in the perspective view in FIG. 2F. The ePTFE then will be pressure and/or heat-treated to sinter the ePTFE. When adhesive is not used, the pressure and/or heat-treating will cause a tight seal to form where the ePTFE overlaps at seam 28.

Figure 2G:
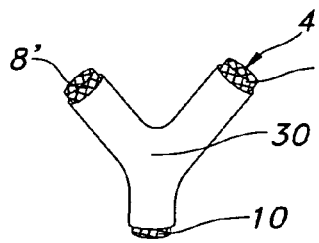

After treatment of seam 28 to form a liquid tight seal, any tape 12 that was used is removed, and graft 30 is formed as shown in FIG. 2G, which is a front view of the graft 30 on mandrel 4. The graft 30 can then be removed from the mandrel 4 (removal not shown).

In the alternative, one or more layers of ePTFE can be added to the graft using the above-described method to form a multi-layered graft prior to removal of graft 30 from mandrel 4. Desirably, at least one reverse wrap-around is used.

Figure 2H:
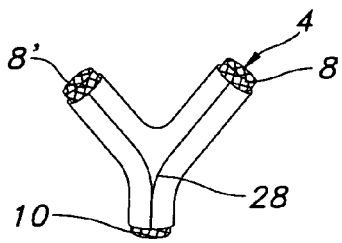
Figure 2I:
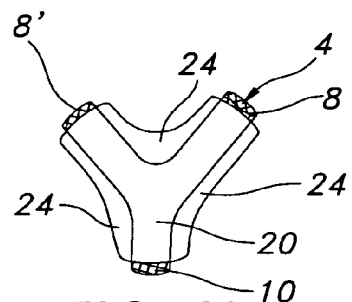
Figure 2J:
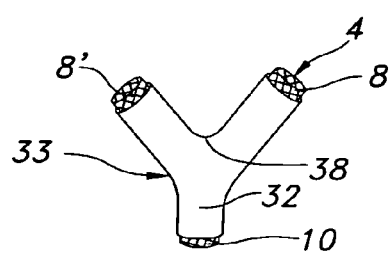
Figure 2K:
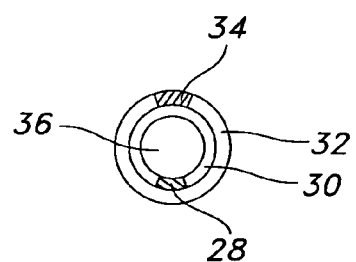

In particular, a reverse wrap-around can be undertaken by rotating the graft 30, as shown in FIG. 2G, 180 degrees such that seam 28 now appears on the front side of the graft as shown in perspective view in FIG. 2H. A shaped form 22 of ePTFE having excess material 24 prepared as described above, and as shown in FIG. 2B, is then placed on the side of the graft having seam 28, such that the a continuous, uninterrupted section of ePTFE covers seam 28, as shown in FIG. 2I. The excess material 24 is then completely wrapped around the graft 30 to form a two-layered graft 33 having a second graft layer 32, as shown in the perspective view in FIG. 2J. In particular, the excess material is completely wrapped around the graft 30 to form a two-layered graft 33 having seams 28 and 34 on opposing sides of the graft and continuous, uninterrupted sections of ePTFE on opposing sides of the graft. Although the underlying graft 30 and the seams 28 and 34 of the two-layered graft 33 cannot be seen in FIG. 2J, both graft layers 30 and 32, the seams 28 and 34, and the graft lumen 36 are apparent in FIG. 2K, which is a cross-section of the trunk of the two-layered graft 32 after removal from mandrel 4. Additional reverse wraps can be undertaken as desired to reinforce further the bifurcation point 38 of the two-layered graft 33 by placing additional layers of continuous, uninterrupted ePTFE thereon.

Alternatively, a graft 30 as shown in FIG. 2G is placed under one or more grafts formed in the same manner as the graft 30 shown in FIG. 2G to form a multi-layered graft. Desirably, the seams of consecutive layers of the multi-layered graft are on opposing sides of the multi-layered graft. A multi-layered graft formed in such a manner is particularly strong at the bifurcation point of the graft as at least one and desirably more than one continuous, uninterrupted section of ePTFE spans that point.

When making such a multi-layered graft, the first few ePTFE sheets may be of sufficient thinness to form a fused seam. Thicker layers of ePTFE sheets 2 may then be applied to increase the strength of the graft. By first adding thin layers and then adding subsequent layers that are of increased thickness relative to the first thin layers, it is possible to obtain a graft that is stronger in the presence of the layers than in the absence of the layers. It should be understood, however, that the thickness of the layers and their positioning in the multi-layered graft of the present invention may be varied in any manner depending on the desire characteristics of the graft.

Formation of Grafts from PTFE Tubular Members

In another aspect of the invention, grafts may be formed from one or more tubular ePTFE member(s). In certain embodiments, the tubular members are formed into shaped forms that can be bonded together to form bifurcated grafts of the subject invention.

In accordance with the subject invention, the tubular member(s) initially may be unsintered, sintered or partially sintered. Partial sintering involves heating the ePTFE at a temperature and for a time which will partially lock the internal polymeric structure of the ePTFE. For partial or complete sintering, heat-treating the ePTFE at a temperature of from about 337° C. to about 398° C. for from about 30 seconds to about 20 minutes is acceptable. Desirably, sintering will be performed at a temperature of from about 343° C. to about 354° C. for from about 2 minutes to about 10 minutes. One having skill in the art will be able to determine appropriate temperature and time ranges for the desired level of sintering for the particular ePTFE tubular member being so treated.

Moreover, the tubular member may be extruded or expanded at the nominal diameter or radially expanded from a tubular member of smaller diameter.

Referring to FIGS. 3A to 3G, another embodiment of the subject invention is shown wherein bifurcated grafts are formed from a single tubular ePTFE member 40. In this embodiment, tubular member 40 as shown in perspective view in FIG. 3A, has a diameter generally equivalent to the intended diameter of a trunk portion of the bifurcated graft of the subject invention. Moreover, a predetermined length of tubular member 40 corresponds to an intended length of a branch portion of the bifurcated graft. As further shown in FIG. 3B, a pinched section 44 of predetermined length l and two branch portions 42 and 42' are formed by pinching the tubular member 40 by means of pressure and/or heat-treatment and thereafter sintering the pinched section 44 to form pinched bifurcated graft form 46.

Figure 3A:
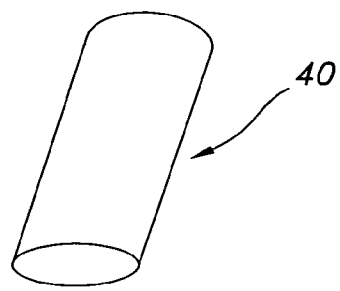
FIGS. 3A to 3G illustrate an embodiment of the subject invention wherein bifurcated grafts are formed from a single tubular ePTFE member.
Figure 3B:
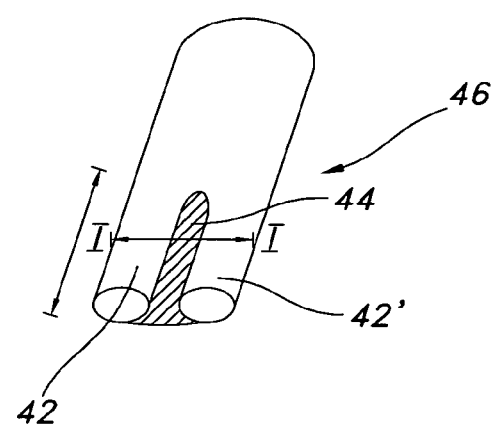
Figure 3C:
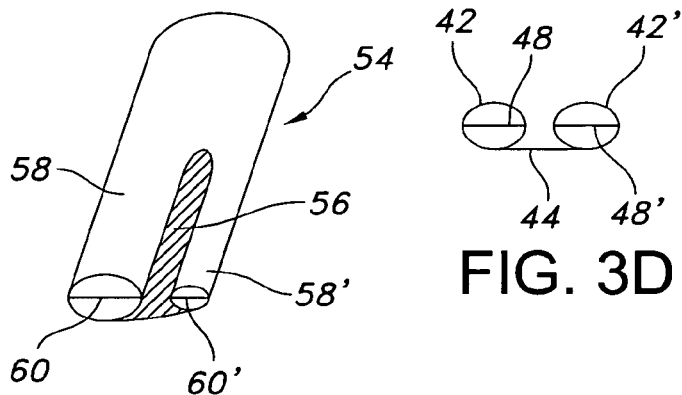
Figure 3D:
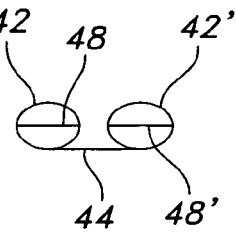
Figure 3E:
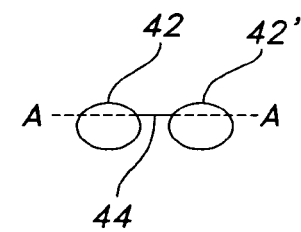

In accordance with this embodiment, tubular member 40 may be pinched such that the diameter of each of the branch portions is either the same or substantially the same as shown in FIG. 3B or substantially different as shown in FIG. 3C. As shown in FIG. 3D, which is a cross-sectional view along line I-I of FIG. 3B of pinched graft form 46, the pinched section 44 is desirably arranged off-center with respect to the diameters 48 and 48' of branch portions 42 and 42'. By forming the pinched section 44 off-center with respect to the diameters 48 and 48' of branch portions 42 and 42', no seam will be present at the bifurcation point of the bifurcated graft end product ultimately formed. Although the pinched section 44 is desirably formed off-center with respect to the diameters 48 and 48' of branch portions 42 and 42', the pinched section 44 also may be formed in a plane A-A which is within the circumferential dimension of branch portions 42 and 42' as shown in FIG. 3E.

Figures 3F, 3G:
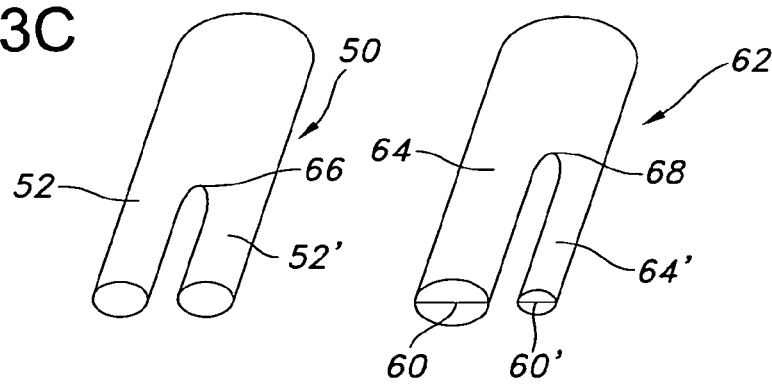

Regarding the pinched graft form 46 shown in perspective view in FIG. 3B, the pinched section 44 is removed from the pinched graft form 46 (e.g., by cutting) thereby forming bifurcated graft 50 having branch portions 52 and 52' of the same or substantially the same diameter, as shown in FIG. 3F (which is a perspective view of the graft 50). Regarding the pinched graft form 54 shown in perspective view in FIG. 3C and having branch portions 58 and 58', the pinched section 56 is removed from the pinched graft form 54 (e.g., by cutting) thereby forming bifurcated graft 62 having branch portions 64 and 64' of unequal diameter 60 and 60' as shown in FIG. 3G (which is a perspective view of graft 62). Although grafts 50 and 62 will both have seams as a result of removing the pinched sections of those grafts, the seam may be positioned such that a continuous, uninterrupted section of ePTFE will still span the bifurcation point 66 of graft 50 and the bifurcation point 68 of graft 62 thus making the grafts particularly strong at their respective bifurcation points.

In another embodiment of the subject invention, grafts formed in accordance with the method described with regard to FIGS. 3A-3G may be used to form multi-layered grafts. In accordance with this embodiment, a graft as shown in FIG. 3F, for example, is placed on a mandrel that conforms to the shape of the graft. A second graft made in the same manner as the graft shown in FIG. 3F may then be placed atop of the first graft. Desirably, the second graft is placed atop of the first graft such that the seams of the two grafts do not overlap. The two grafts are then pressure and/or heat-treated to form a reinforced unitary bifurcated graft structure of the invention. The reinforced bifurcated graft so formed may be used in combination with one or more other bifurcated grafts of the invention, or part thereof, to provide, for example, a doubly, triply or quadruply reinforced bifurcated graft of the subject invention.

Referring to FIGS. 4A to 4E, an embodiment of the subject invention is shown in which two tubular ePTFE members are used to form a bifurcated graft of the subject invention. In accordance with this embodiment, a first tubular member 70 is provided. The first tubular member 70, as shown in perspective view in FIG. 4A, has a diameter generally equivalent to the diameter of the trunk of a desired bifurcated graft. A second tubular member 72 is provided having a diameter which is generally equivalent to the diameter of the branches of that same desired bifurcated graft. A perspective view of the second tubular member 72 is shown in FIG. 4B. The tubular members may either be made to size or radially expanded to size. For applications involving use with braided stents, at least the second tubular member 72 is radially expanded to the desired diameter prior to assembly into a bifurcated graft. More desirably, both first and second tubular members 70 and 72 are radially expanded to desired diameters prior to assembly.

With further reference to FIGS. 4A to 4E, the first and second tubular members 70 and 72 are desirably made from ePTFE. Desirably, the first and second tubular members 70 and 72 are made from ePTFE that has been bonded to a textile, such as a stretch knit, weave or braid.

In the embodiment shown in FIGS. 4A to 4E, the first and second tubular members 70 and 72 are desirably pre-formed such that the ePTFE has a substantially uniform or a uniform node and fibril microstructure. After this pre-forming step, a hole 74 is formed in second tubular member 72 as shown in FIG. 4B.

Opposed ends of second tubular member 72 then are bent upward, in the direction shown by the arrows in FIG. 4B, and the hole 74 is stretched using any suitable tool (such as a waist tool) to form an opening 76 that has substantially the same diameter as first tubular member 70 and that is suitable for placement on a mandrel 4. As a result of these steps, a shaped graft form 78 having branches 80 and 80' as shown in FIG. 4C is formed. The cut-away which forms hole 74 is desirably carved out in a manner which permits a continuous, uninterrupted crotch portion to be formed when the opposed ends of tubular member 72 are positioned to form branches 80 and 80' as shown in FIG. 4C.

Tubular member 70 and shaped graft form 78 are then arranged on a mandrel 4 so as to form a bifurcated graft. As shown in the perspective view of FIG. 4D, mandrel 4 has branches 8 and 8' and a trunk 10. More particularly, shaped graft form 78 is first placed on mandrel 4 as shown in FIG. 4D. Tubular member 70 then is slid over branches 8 and 8' of mandrel 4 having shaped graft form 78 already in place and down to trunk section 10 of mandrel 4 to form a bifurcated graft form 82 of the subject invention as shown on mandrel 4 in FIG. 4D. As shown in FIG. 4D, bifurcated graft form 82 has a section 84 where shaped graft form 78 and tubular member 70 overlap. Desirably, approximately 0.25 inches of shaped graft form 78 overlaps with tubular member 70. In the alternative, tubular member 70 may first be placed on the trunk 10 of mandrel 4, and shaped graft form 78 then slid thereon to form overlapping section 84.

Next, overlapping section 84 is treated so as to form a liquid-tight seal. There are no particular limitations to the manner in which the overlapping section 84 is treated to form the seal. For example, the overlapping section 84 of shaped graft form 78 and tubular member 70 can be welded together, sintered together, bonded together using adhesion, laminated together, or stitched or otherwise sewn together. Desirably, heat-treating is performed to sinter completely the bifurcated graft form to achieve the bifurcated graft end product 86. Desirably, sintering may be performed at about 352° C. for about 5 to about 30 minutes and more desirably from about 10 to about 20 minutes. Pressure may optionally be used in conjunction with heat. Optionally, tape 12, such as Teflon™ tape, may be wrapped radially about overlapping section 84 as shown in FIG. 4D prior to sintering bifurcated graft form 82. After sintering, the resultant bifurcated graft form 86 is removed from the mandrel 4. When tape 12 is used, the tape 12 is removed from the bifurcated graft form end product 86 after the heat-treating step. A front view of the bifurcated graft end product 86 is shown in FIG. 4E.

Referring to FIGS. 5A to 5K, an embodiment of the subject invention is shown wherein three ePTFE tubular members are used to form a bifurcated graft having a bifurcation point that is spanned by four layers of continuous, uninterrupted ePTFE. In this embodiment, a first ePTFE tubular member 88 as shown in perspective in FIG. 5A is provided. Tubular member 88 has a diameter generally equivalent to the diameter of a trunk of a desired bifurcated graft. Second and third ePTFE tubular members, 90 and 92, as shown in perspective in FIG. 5B, also are provided with tubular member 90 having a diameter that is generally equivalent to the diameter of one branch of a desired bifurcated graft and the other tubular member 92 having a diameter that is generally equivalent to the diameter of the other branch of the desired bifurcated graft. Second and third tubular members 90 and 92 may have the same or different diameters. Tubular members 88, 90, and 92 can be made to size or radially expanded. Desirably, at least one of tubular members 88, 90, and 92 is radially expanded to its intended diameter prior to assembly into a bifurcated graft. More desirably, each of tubular members 88, 90, and 92 is radially expanded prior to assembly into a bifurcated graft in accordance with this embodiment of the subject invention.

In order to form a graft of the invention according to the embodiment shown in FIGS. 5A to 5K, the ePTFE tubular members 88, 90, and 92 are pre-formed to have uniform or substantially uniform node and fibril structures. After this initial pre-forming step, one end of the second tubular member 90 is stretched to form a shaped member 91 having a flared or substantially-flared end 94 as shown in perspective view in FIG. 5C. Likewise, one end of the third tubular member 92 also is stretched to form a shaped member 93 having a flared or substantially-flared end 96, as also shown in perspective view in FIG. 5C. A mandrel 4 having a bifurcation point 6, a trunk portion 10, two branches 8 and 8', and a waist 81 is then provided as shown in perspective view in FIG. 5D. Shaped member 91 is then slid onto a branch 8 of the mandrel 4 such that at least part of the flared section 94 of the shaped member 91 covers the bifurcation point 6 of the mandrel 4 as shown in the perspective view in FIG. 5E. Shaped member 93 is then slid onto the other branch 8' of mandrel 4 such that the flared section 96 of the shaped member 93 at least partially overlaps a portion of the shaped member 91 at the bifurcation point 6 of mandrel 4 to form intermediate graft shape 100 as further shown in FIG. 5E. As shown in FIG. 5E, the overlapping section 98 covers the bifurcation point 6 of the mandrel 4. Although FIG. 5E only shows overlapping section 98 on the front side of the intermediate graft shape 100, it will be understood that overlapping section 98 also appears on the back side (not shown) of the intermediate graft shape 100.

The first tubular member 88 is then cut so as to form two opposing flaps 102 and 104 on one end of the tubular member and a trunk portion 106 to form shaped member 108 as shown in perspective view in FIG. 5F. As further shown in FIG. 5F, opposing flap 102 has a tail 110, and opposing flap 104 has a tail 112. Shaped member 108 is then pulled up and onto the trunk 10 of mandrel 4 until the opposing flaps 102 and 104 are positioned between the branches 8 and 8' of the mandrel 4 in a manner that will allow each of the flaps 102 and 104 to be folded between the branches so that the tail 110 of flap 102 is ultimately tucked within and under the other flap 104. A perspective view of the front side of an intermediate graft product 101 so formed is shown in FIG. 5G on mandrel 4.

Next, flap 102 is folded over the bifurcation point 6 of the mandrel 4 and tucked in on the opposite side of the mandrel 4 (having shaped members 91 and 93 thereon) such that its tail 110 is positioned between the trunk portion 106 of shaped member 108 and overlapping section 98 on the back side of mandrel 4. A perspective view of the front side of an intermediate graft product 114 so formed in shown in FIG. 5H. Then, flap 104 is folded over the bifurcation point 6 of the mandrel 4 (having shaped members 91 and 93 thereon) such that its tail 112 covers already folded flap 102 as shown in FIG. 5I, which is a front perspective view of the intermediate graft product 116 so formed.

Thereafter, the intermediate graft product 116 is treated so as to form a unitary bifurcated graft of the invention. Desirably, tape 12, such as Teflon™ tape, is wrapped radially around the waist 81 of the mandrel 4 (having shaped members 91, 93 and 108 thereon), as shown in the front perspective view of FIG. 5J, to provide pressure at the sections of the graft where flaps 102 and 104 cover overlapping section 98. The wrapped graft form is then pressure and/or heat-treated to sinter the graft form to achieve a unitary bifurcated graft. After pressure and/or heat-treating, tape 12 is removed, and the resultant bifurcated graft 117 is removed from the mandrel 4. A perspective view of the bifurcated graft after removal from the mandrel 4 is shown in FIG. 5K. The bifurcated graft shown in FIG. 5K has four layers of continuous, uninterrupted ePTFE that span at least the bifurcation point 119 of the graft. In view of such quadruple reinforcement at the bifurcation point 119, such a graft is particularly strong at that point.

Figure 6A:
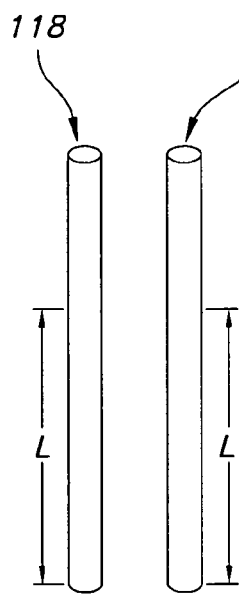
FIGS. 6A to 6E illustrate an embodiment of the subject invention wherein two ePTFE shaped forms are used to form a two-layered bifurcated graft form of the subject invention.

Referring to FIGS. 6A to 6E, an embodiment of the present invention is shown in which two ePTFE tubular members are used to form a bifurcated graft of the subject invention. In this embodiment, first and second tubular members, 118 and 120, as shown in the perspective view in FIG. 6A, are provided, with each having a diameter generally equivalent to the diameter of a branch of a desired bifurcated graft. First and second tubular members 118 and 120 may have the same or different diameters. First- and second tubular members 118 and 120 are then radially expanded at a predetermined portion thereof, L and L', so that the radially expanded portions 122 and 124, as shown in the perspective view in FIG. 6B, each have a diameter that is generally equivalent to the diameter of a trunk of a desired bifurcated graft. As further shown in FIG. 6B, a transition point 126 and 128 results where the diameter of each of the tubular members changes after radial expansion of a predetermined portion thereof.

Figure 6B:
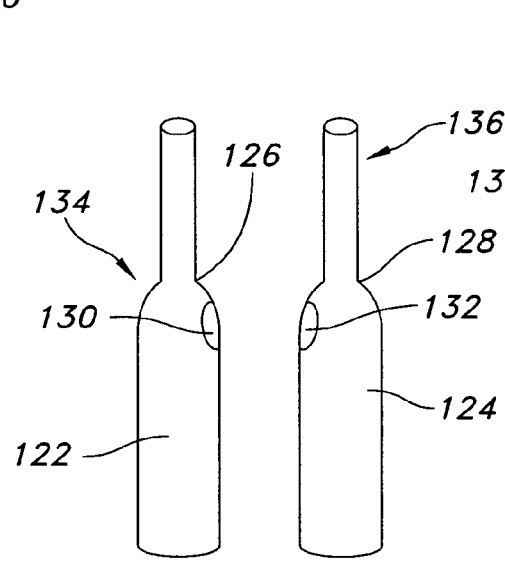

As shown in perspective view in FIG. 6B, circular cut-outs 130 and 132 are made in the radially expanded portion of each tubular member proximal to transition points 126 and 128 to form shaped members 134 and 136. Next, shaped tubular member 134 is arranged over first branch 8 of mandrel 4 such that cut-out 130 fits over the second branch 8' of mandrel 4 and such that the radially expanded portion 122 surrounds the trunk 10 of the mandrel 4 as shown in perspective view in FIG. 6C. Shaped tubular member 136 then is arranged over the second branch 8' of mandrel 4 such that cut-out 132 fits over the first branch 8 of mandrel 4 and such that the radially expanded portion 124 surrounds the trunk 10 of the mandrel 4 to form the intermediate graft form 138, which is shown on mandrel 4 in perspective view in FIG. 6D. As shown in FIG. 6D, the intermediate graft form 138 has branches 160 and 160' and a trunk 158. The intermediate graft form 138 formed by such steps then may be sintered and removed from mandrel 4 so as to form a bifurcated graft 140 having a trunk 142 and branches 144 and 144' as shown in FIG. 6E. A bifurcated graft formed in such a manner is particularly strong at the bifurcation point 146 of the graft as two layers of continuous, uninterrupted ePTFE span that point.

Figure 6C:
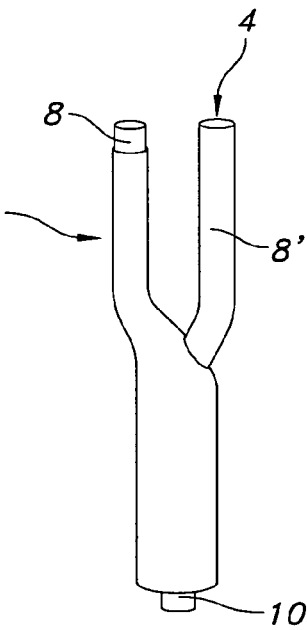
Figure 6D:
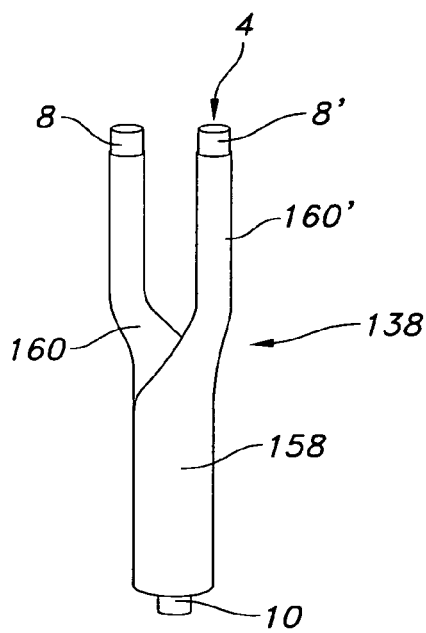
Figure 6E:
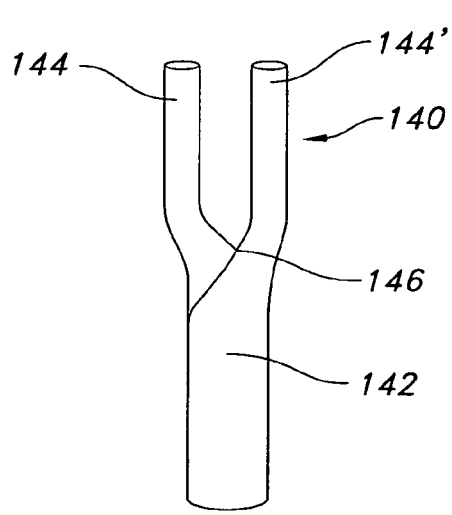

Moreover, additional shaped members as shown in FIG. 6B can be added to the bifurcated graft 140 by means of the steps described with regard to FIGS. 6C-6D so that additional layers of continuous, uninterrupted ePTFE span the bifurcation point and thus provide further reinforcement thereto.

Referring to FIGS. 7A-7E, in another embodiment of the subject invention, an intermediate graft form 138 as shown in FIG. 6D is further reinforced with a graft form 148 as shown in perspective view in FIG. 7B. A shaped form 148 as shown in FIG. 7B is first made from a single ePTFE tubular member 150 as shown in perspective view in FIG. 7A. In particular, after the tubular member 150 has been preformed such that the ePTFE has a substantially uniform or a uniform node and fibril microstructure, a hole 152 is formed therein as shown in FIG. 7A. Opposed ends of the tubular member 150 are then bent upward, in the direction shown by the arrows in FIG. 7A, to form the shaped form 148 having branches 164 and 164' as shown in perspective view in FIG. 7B. Thereafter, the hole 152 is stretched using any suitable tool (such as a waist tool) to form a shaped graft form 154 having an opening 156 that has substantially the same diameter as the trunk 158 of the intermediate graft form 138 shown in FIG. 6D.

Graft form 154, shown in perspective view in FIG. 7C, is then slid over the branches 160 and 160' of the intermediate graft form 138 shown in FIG. 6D to form the intermediate graft form 162 shown in FIG. 7D on a mandrel 4 having branches 8 and 8' and a trunk 10. As shown in perspective view in FIG. 7D, the intermediate graft form 162 has branches 164 and 164', a trunk 168, and a bifurcation point 188. The intermediate graft form 162 is then sintered and removed from mandrel 4 to form the bifurcated graft 171 shown in perspective view in FIG. 7E. The bifurcated graft 171 shown in FIG. 7E is triply reinforced with ePTFE at the bifurcation point 170 of the graft.

Referring to FIGS. 8A-8E, in another embodiment of the subject invention, a graft form 162 as shown in FIG. 7D is further reinforced with a shaped form 172, a back perspective view of which is shown in FIG. 8B and a front perspective view of which is shown in FIG. 8C. In this embodiment, a tubular member 174 of ePTFE as shown in perspective view in FIG. 8A is provided. The tubular member 174 has a diameter that generally corresponds to the diameter of the trunk 168 of the graft form shown in FIG. 7D. Next, a hole 178 as shown in FIG. 8A is formed in tubular member 174 to form shaped tubular member 180. As shown in FIG. 8A, shaped tubular member 180 has a first end 182, a second end 184, and a strip 186 interposed therebetween as a result of the hole 178 being formed therein.

Next, shaped tubular member 180 is folded along strip 186. Then, the first end 182 of the shaped tubular member 180 is tucked into the second end 184 such that first end 182 is positioned within the second end 184 to form shaped form 172.

Shaped form 172 then may be slid over the intermediate graft form 162 shown in FIG. 7D such that branches 8 and 8' of mandrel 4 shown in FIG. 7D are arranged on either side of strip 186, while strip 186 covers and reinforces the bifurcation point 188 of the intermediate graft form 162. FIG. 8D is a perspective view of the resultant intermediate graft form 190 as shown on mandrel 4. Next, tape 12, such as ePTFE plumbing tape, can optionally be wrapped around the ends 194 and 194' of branches 164 and 164', around the crotch section 192, and around the end 196 of shaped form 172, as shown in FIG. 8D.

Thereafter, the graft form 190 is sintered and any tape 12 removed. Desirably, the four ePTFE shaped forms are sintered together at about 352° C. for about 5 to about 30 minutes, and more desirably from about 10 to about 20 minutes. The resultant bifurcated graft form end product 198, shown in perspective view in FIG. 8E after removal from mandrel 4, is quadruply reinforced with ePTFE at the bifurcation point 200 of the graft.

With further reference to the embodiments illustrated in FIGS. 6A-8E, it is useful, when adding a shaped form of ePTFE to another shaped form of ePTFE, to use directed heat, such as from a heat gun or other apparatus to secure the shaped forms together prior to sintering. When the desired number of shaped ePTFE forms has been compiled on a mandrel to form an intermediate graft form, tape or other securement can be added to the intermediate graft form, as discussed above with regard to FIG. 8D, to secure the intermediate graft to itself and to the mandrel. The resultant intermediate graft form is then sintered and allowed to cool. Desirably, the intermediate graft form may be sintered together at about 352° F. for about 5 to about 30 minutes and more desirably from about 10 to about 20 minutes to achieve the desired graft end product, as also discussed with regard to FIG. 8D.

Referring to FIGS. 9A-9G, another embodiment of the subject invention is shown wherein a bifurcated graft is formed from two shaped forms. In this embodiment, an ePTFE tubular member 202, as shown in the perspective view in FIG. 9A, is provided. The tubular member 202 may be pre-formed to have a uniform or substantially uniform node and fibril structure and has a diameter that corresponds to the diameter of a trunk of a desired bifurcated graft to be formed therefrom. A shaped form 204 is formed by stretching the tubular member 202 shown in FIG. 9A to form a tubular member having a flared or substantially flared end 206 as shown in the front view of FIG. 9B. A mandrel 4 having branches 8 and 8', a trunk 10, a waist 81, and crotch section 210, as shown in the perspective view of FIG. 9C, is then provided.

Next, two flared ePTFE members 214 and 216 are formed and fitted onto mandrel 4 in the same manner described above with regard to FIGS. 5A-5E to form shaped form 212, which is shown in perspective view on mandrel 4 in FIG. 9D. As shown in the perspective view in FIG. 9D, an overlapping section 218 is formed where tubular members 214 and 216 overlap. Shaped form 204 may then be positioned on the trunk 10 of the mandrel 4 such that the flared end 206 covers the overlapping section 218 of shaped form 212 and such that at least a portion of the flared end 206 covers at least a portion of the branches 8 and 8' of the mandrel 4, as shown in the perspective view of FIG. 9E. The portion of the flared end 206 that covers at least a portion of the branches 8 and 8' may then be folded over the crotch section 210 of the underlying mandrel 4 to form the intermediate graft form 220 shown in perspective view in FIG. 9F. Next, a tape, such as Teflon™ tape 12, may be wrapped radially around the ePTFE that covers the waist 81 of the mandrel 4 as further shown in FIG. 9F. Thereafter, the intermediate graft form 220 is sintered and the tape 12 removed to form the bifurcated graft 222 shown after removal from the mandrel 4 in perspective view in FIG. 9G. The bifurcation point 208 of bifurcated graft 222 is spanned by three continuous, uninterrupted sections of ePTFE.

Referring to FIGS. 10A-10F, another embodiment of the subject invention is shown wherein a bifurcated graft may be formed from two shaped forms. In this embodiment, a mandrel 4 having branches 8 and 8', a trunk 10, a waist 81, and a crotch section 210, as shown in perspective view in FIG. 10A, is provided.

Next a shaped form 224 having branches 226 and 226', as shown in perspective view in FIG. 10B, is provided. The shaped form 224 is formed in the same manner described above with regard to FIGS. 7A-7C, and has a diameter of the trunk of a desired bifurcated graft. Also provided is a shaped form 228 having a flared end 230 as shown in FIG. 10C. Shaped form 228 is made in the same manner as described above with regard to FIG. 9B. In this embodiment, shaped form 224 is positioned on mandrel 4 such that the branches 226 and 226' of the shaped form 224 are positioned on branches 8 and 8' of the mandrel 4, as shown in the perspective view in FIG. 10D. Shaped form 228 is then positioned on the trunk 10 of mandrel 4 such that at least a portion of the flared end 230 extends between branches 8 and 8' of mandrel 4, as further shown in FIG. 10D. The portion of the flared end 230 that extends between the branches 8 and 8' is then folded over the crotch section 210 of the underlying mandrel 4, having shaped form 224 thereon, to form the intermediate graft form 231 shown in FIG. 10E. Next, a tape 12, such as Teflon™ tape, can be wrapped radially around the ePTFE that covers the waist 81 of the mandrel 4 as further shown in FIG. 10E. Thereafter, the intermediate graft form 231 is sintered and the tape 12 removed to form the bifurcated graft 232 shown after removal from mandrel 4 in perspective view in FIG. 10F.

Referring to FIGS. 11A-11E, another embodiment of the subject invention is shown wherein two sheets of ePTFE are combined with a shaped form of the subject invention to form a bifurcated graft. As shown in the perspective view in FIG. 11A, a sheet 2 of ePTFE is positioned on a mandrel 4 having branches 8 and 8' and a trunk 10 in the same manner as described above with regard to FIGS. 1A-1B. Next, a bifurcated graft form 233, a back view of which is shown in the perspective view in FIG. 11B, is positioned on the mandrel 4 as shown in FIG. 11B. As shown in FIG. 11B, the bifurcated graft form 233 has a seam 234 formed thereon. The bifurcated graft form 233 is desirably formed in the same manner described above with regard to FIGS. 2A-2H. Another sheet 2 of ePTFE is then positioned on the mandrel 4 atop of the bifurcated graft form 233 as shown in the perspective view in FIG. 11C. Thereafter, tape 12, such as Teflon™ tape, is desirably wrapped around the three layers as further shown in FIG. 11C to secure the layers to the mandrel 4. The three layers are then sintered. Next, any excess ePTFE is trimmed from the ePTFE sheets 2 to form the bifurcated graft 236 shown in perspective view in FIG. 11D on mandrel 4. FIG. 11E shows a perspective view of the three-layered, bifurcated graft 236 after removal from the mandrel 4. As the outer layer of the bifurcated graft 236 is seamless, blood will be more apt to flow smoothly thereon upon incorporation of the graft into the blood vessel of a body.

With further reference to FIGS. 11A-11E, although bifurcated graft form 233 was positioned between two sheets of ePTFE, it should be understood that any tubular member, shaped form or graft form made in accordance with the subject invention, or any combination thereof, can be positioned between the two sheets in addition to, or in the alternative to, bifurcated graft form 233. By adding additional tubular members, shaped forms or graft forms to a graft already positioned between the two sheets, it is possible to impart additional strength to the bifurcated graft end product.

Moreover, although certain particularly desirable embodiments of the invention have been discussed herein, it should be understood that when various tubular members and/or shaped forms are used to form a unitary, multi-furcated graft of the subject invention, the tubular members and/or shaped forms can be added to a mandrel in any order during formation of such a multi-furcated graft of the subject invention.

By forming bifurcated grafts of the subject invention from at least two separate ePTFE members, as exemplified, for example, in numerous embodiments above and particularly shown in FIGS. 9A-9G and 10A-10F, it is possible to achieve bifurcated grafts having optimal porosity and handling characteristics.

Stent-Grafts of the Invention

Any suitable stent may be used in combination with the multi-furcated grafts of the subject invention to form multi-furcated stent-grafts of the invention, such as bifurcated stent grafts. Various stent types and stent constructions may be employed in the subject invention including, without limitation, self-expanding stents and balloon expandable stents. The stents may be capable of radially contracting as well. Self-expanding stents include those that have a spring-like action which causes the stent to expand radially. Such stents include, for example, stents made from elgiloy. Alternatively, stents may be used which expand due to the memory properties of the stent material for a particular configuration at a certain temperature. Such stents include, for example, stents made from nitinol. Moreover, other materials known to those of skill in the art can be used and include, for example, stainless steel, platinum, gold, titanium, tantalum, niobium, and other biocompatible materials, including biocompatible polymeric materials. Stents made from polymeric materials include, for example, woven or braided polymeric stents.

The stent for use in the stent-grafts of the subject invention may have any suitable configuration. In particular, the configuration of the stent may be chosen from a host of geometries. For example, wire stents can be fastened in a continuous helical pattern, with or without wave-like forms or zigzags in the wire, to form a radially deformable stent. Individual rings or circular members can be linked together such as by struts, sutures, or interlacing or locking of rings to form a tubular stent. Examples of suitable stent configurations can be found, for example, in U.S. Pat. Nos. 4,994,071 and 5,342,387, which are incorporated herein by reference. An example of a commercially available stent useful in the subject invention is a braided self-expanding stent referred to as Wallstent® and available from SciMed Life Systems, Inc., Maple Grove, Minn.

The stent-grafts of the subject invention thus include at least one graft layer on the inside and/or outside of a stent structure. For example, a bifurcated stent-graft of the subject invention may include an ePTFE graft or other ePTFE tubular component made in accordance with the subject invention positioned on the inside and/or outside surface of the stent. Desirably, the stent-grafts of the subject invention have at least one ePTFE bifurcated graft of the invention, or a component thereof, placed on an outer and/or inner surface of a stent.

It is advantageous to use stent-graft configurations in accordance with the subject invention because the stent helps provide and ensure the patency of the stent-graft combination, while the vascular graft, particularly when used as a liner of a blood vessel, renders the vessel more conducive to unobstructed blood flow.

More than one stent may be employed. For example, two or more stents may be used separately and/or joined together to form the branched support structure.

Methods of Making Bifurcated Stent-Grafts

Referring to FIGS. 12A to 12K, a stent-graft according to the invention may be formed by first positioning a four-layered, bifurcated graft 250 on a mandrel 4 having branches 8 and 8' and a trunk 10 as shown in the perspective view in FIG. 12A.

Desirably, the bifurcated graft may be made in the same manner as the four-layered graft shown in FIG. 8E. Although a four-layered graft is shown in FIG. 12A, it should be understood that suitable grafts include, for example, any bifurcated graft made in accordance with the subject invention. The ends 252 of the graft 250 then are secured using tape 12, such as Teflon™ tape.

A stent 244, which is shown for purposes of illustration as a braided stent, is then provided as shown in the perspective view in FIG. 12B. As shown in FIG. 12B, the stent 244 has branches 246 and 246' and a trunk 248. The stent 244 may then be radially compressed along line B-B shown in FIG. 12B. Thereafter, another four-layered graft 254 of the subject invention is slid over stent 244, as shown in the perspective view in FIG. 12C. Desirably, the graft is a four-layered graft made in the same manner as the graft shown in FIG. 8E. The stent 244 is released from the radially compressed state and allowed to expand to a free state at room temperature. The stent 244 with graft form 254 thereon is then positioned on the mandrel 4 atop of the graft form 250 to form stent-graft form 271, which is shown on mandrel 4 in the perspective view in FIG. 12D. As shown in FIG. 12D, stent-graft form 271 has branches 268 and 268' and a trunk 270. Although FIGS. 12B-12C illustrate graft form 254 being placed on a stent 244 prior to assembly on a mandrel, it should be understood that stent 244 may first be placed on the mandrel 4 having a graft form 250 thereon and the graft form 254 then positioned thereon.

The trunk portion 248 of the stent 244 is then pulled in a direction distal to the trunk of the mandrel 4, as shown by the arrow in FIG. 12E, along the axis defined by line C-C, to compress the trunk portion 248 of the stent 244 to the diameter of the trunk portion 10 of mandrel 4. The end of the trunk 248 of the stent 244 is then desirably wrapped with tape 12, such as Teflon™ tape, as also shown in FIG. 12E.

Thereafter, branch portion 246 of the stent 244 may then be pulled axially along line D-D in the direction shown by the arrow in the perspective view in FIG. 12F, and branch portion 246' of the stent 244 may then be pulled axially along line E-E in the direction shown by the arrow in FIG. 12F to compress each of the branch portions 246 and 246' of the stent 244 to the diameter of corresponding branches 8 and 8' of mandrel 4. Desirably, the ends of the branch portions 246 and 246' of the stent 244 may then be secured in place, using tape 12, such as Teflon™ tape, as also shown in FIG. 12F. Although FIGS. 12A-12F show a stent 244 positioned between two ePTFE bifurcated grafts, the order of steps recited above may be reversed, so as to place the stent 244 over the mandrel 4 first and then place bifurcated grafts 250 and 254 or any other grafts of the subject invention onto the mandrel 4 atop of the stent 244.

Silicone 258 may be wrapped helically around each branch 8 and 8' and the trunk 10 of the mandrel 4 atop the bifurcated graft 250, stent 244, and bifurcated graft 254 that were positioned thereon, as shown in the perspective view in FIG. 12G, to form a silicone wrap. The ends of the silicone wrap then may be secured using tape 12, such as Teflon™ tape or the like, as also shown in FIG. 12G. Desirably, the mandrel 4 with graft layer 250, stent 244, and graft layer 254 thereon may be wrapped several times with silicone 258 prior to securing the silicone 258 with tape.

Additional silicone 258, including at least some pre-melted silicone, may then be packed between the branches 8 and 8' in the crotch 260 and lower stomach 262 area, as shown in FIG. 12G, to eliminate any gaps therein and to prevent the branches 268 and 268' of stent-graft form 271 from contacting one another during subsequent heat-treating of the stent-graft combination. Thereafter, trunk 270 of stent-graft form 271 may be wrapped a number of times with silicone 258 and the ends of the silicone wrap may be secured using tape 12, such as Teflon™ tape or the like, as shown in the perspective view in FIG. 12G. The silicone 258 serves a load-bearing function to distribute pressure evenly during heat-treating of the stent-graft combination as described herein.

Referring to FIG. 12H, one or more heat-shrinkable ePTFE tubes 264 and 264', sized large enough to fit over the branches of the radially compressed stent-graft form 271, may then be placed over the silicone-covered branches 276 and 276' of the stent-graft form 271. The heat-shrinkable ePTFE tubes 264 and 264' may then be heat-treated so that they shrink and assume the contour of the silicone-covered branches 276 and 276' of the stent-graft form 271.

A heat-shrinkable ePTFE tube 266 sized large enough to fit over the silicone-covered trunk 278 of the stent 244 may then be placed over the silicone-covered trunk 278 of the stent-graft form 271 as shown in the perspective view in FIG. 12H. The heat-shrinkable ePTFE tube 266 may then be heat-treated so that it shrinks and assumes the contour of the silicone-covered trunk 278 of the stent-graft form 271. Thereafter, a heat-shrinkable tube 268 may be placed over the entire trunk and branches and shrunk to size as shown in the perspective view in FIG. 12J. In some embodiments, where heat-shrinkable tubing is used, it may be desirable to place more loosely fitting tubing over tighter-fitting tubing.

The heat-treating or laminating steps can include a plurality of heat treatments at about 352° C. to about 370° C. Desirably, the heat-treating or laminating steps include a plurality of heat treatments at about 365° C. for about 5 to about 30 minutes and more desirably for about 10 to about 20 minutes. As a result of the heat-treating, the silicone desirably acts as a medium for transferring the compressive force from the heat-shrink tubing to the underlying ePTFE graft layers 250 and 254. In some embodiments, the silicone may conform the ePTFE around the stent structure 244.

After heat-treating and subsequent cooling, the heat-shrinkable tubing 264, 264', and 266 and silicone 258 are removed to form a bifurcated stent-graft 280 having branches 272 and 272' and a trunk 274 as shown in the perspective view in FIG. 12J on mandrel 4. A stent-graft 280 so formed may be removed from the mandrel 4 by pushing the stent-graft 280 towards the branches 8 and 8' of mandrel 4. FIG. 12K shows the stent-graft 280 after removal from mandrel 4. A stent-graft 280 so formed may be expanded radially by applying localized heat and axially compressing the stent along line F-F shown in FIG. 12K.

In a manner similar to that process described with respect to the embodiments of FIGS. 12A-K, the embodiments of other Figures shown may also be made into a stent-graft.

In another embodiment of the subject invention, the grafts or stent-grafts according to the invention may be formed using a pressure oven. In such an embodiment, a perforated vacuum tube is operably connected to a vacuum supply. A bifurcated silicone sleeve, then is arranged inside the perforated vacuum tube. A negative pressure is applied to the vacuum tube and serves to expand the silicone sleeve in the vacuum tube. Upon expansion, a mandrel having a bifurcated graft intermediate made from at least two different shaped forms of the subject invention, and optionally a stent placed thereon, is arranged inside the silicone sleeve to form a sleeved assembly. The vacuum inside the vacuum tube may be released at this time.

Next, the sleeved assembly is placed into a pressure oven. Heat treatment is then performed while pressure oven is placed under positive pressure. Desirably, the pressure is maintained in a range of from about 3 psi to about 100 psi. Desirably, a heat treatment cycle of repeated heating and cooling periods is then performed at temperatures and for a time sufficient to permit complete sintering of the graft material and to complete lamination of the graft to stent, if a stent is present. Application of pressure and heat assures that the graft intermediate (or stent-graft) of the invention conforms to the shape of the mandrel. After the heat-treating cycle, the silicone sleeve is removed from the oven, and the bifurcated graft end product is removed from the mandrel.

In another particularly useful embodiment of the subject invention, a stent 244 having branch portions 246 and 246' and trunk 248 as shown in FIG. 12B, is placed atop of a mandrel 4 having tubular members 91 and 93 placed thereon as shown in FIG. 5E. The shaped member 108 shown in FIG. 5F then can be placed on the trunk 248 of bifurcated stent 244 in a manner as described with regard to FIGS. 5G-5K.

Moreover, it is particularly useful, for example, to position a bifurcated stent 244, as shown in FIG. 12B, atop of the mandrel 4 shown in FIG. 9D, which has tubular members 214 and 216 placed thereon. Shaped member 204 shown in FIG. 9B then can be placed on the trunk 248 of the stent 244 in a manner as described with regard to FIGS. 9E to 9G. Such an assembly may then be sintered to form a stent-graft of the subject invention.

Likewise, it also is particularly useful, for example, to position a bifurcated stent 244, as shown in FIG. 12B, atop of mandrel 4 having a shaped form 224 as shown in FIG. 10B thereon. Shaped member 228 shown in FIG. 10C may then be placed on the trunk 248 of the stent 244 in a manner as described with regard to FIGS. 10D to 10F. Such an assembly may then be sintered to form a stent-graft of the subject invention.

Furthermore, it also is particularly useful, for example to position a bifurcated stent 244, as shown in FIG. 12B, atop of a mandrel 4 having a bifurcated graft 140 as shown in FIG. 6E thereon. Shaped graft form 154 as shown in FIG. 7C may then be placed on stent 244 in a manner described with regard to FIGS. 7D-7E. Additionally, or in the alternative, a shaped member 172 as shown in FIGS. 8B-8C may be placed on the trunk 248 of the stent 244 in a manner as described with regard to FIG. 8D.

With some embodiments, such as those identified in FIGS. 10A-10F, it is possible to minimize the number of sintering steps needed. For example, as the outer and/or inner layers of the grafts may be sintered as a unit with the stent rather than individually before placement on the stent, one or sintering steps may be saved. As discussed above with respect to certain of the embodiments, it is desirable to sinter graft-forms and stent-graft forms of the subject invention at about 352° C. for about 5 to about 30 minutes and more desirably for about 10 to about 20 minutes.

Lamination Method Using Dies

In another embodiment of the invention, ePTFE tubular members and other ePTFE shaped forms that are used to form bifurcated graft intermediates, or portions thereof, may be joined together using dies. In particular, the dies are used, in conjunction with heat and pressure, to apply a lamination or "bonding force" to a particular area by spot or local welding. By using such dies, it is possible to maintain the properties of the ePTFE at the site of welding.

Desirably, the contour of the die matches or substantially matches the contour of the area to be joined together. Thus, for example, overlapping section 84 shown in FIG. 4E, can be bonded together using a die that conforms to the contour of the intermediate graft form 82 shown in FIG. 4D at and around the overlapping section 84.

Figure 13:
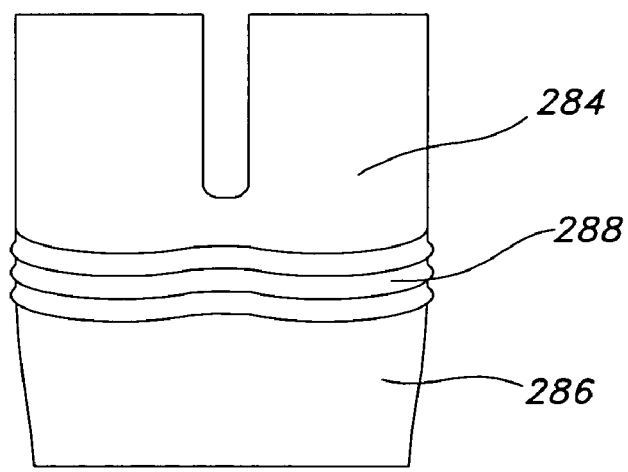
FIG. 13 is a photograph of two ePTFE shaped forms that have been welded together using a lamination method of the subject invention.

A photograph of two ePTFE shaped forms 284 and 286 that have been welded together using the aforementioned method is shown in FIG. 13. As shown in FIG. 13, impressions 288 from the welding will result in the ePTFE at the area of welding.

In accordance with the subject invention, it may be useful to employ at least two dies sets to complete welding around the circumference of a bifurcated graft intermediate, or portion thereof, of the subject invention. For example, one die set can be employed for the front and back portions of a bifurcated graft intermediate while another die set can be employed for the sides of the bifurcated graft intermediate.

The die can have any suitable configuration. For example, the die can include stripes, zig-zags, small points, a sinusoidal shape, or a crossover stripes configuration. By employing dies having such configurations, it is possible to maintain the flexibility of the ePTFE material that surrounds the weld.

Moreover, in accordance with the subject invention, dies as discussed above can be employed in the selective lamination of ePTFE layers that are placed on the inner and/or outer graft layers of a stent-graft of the subject invention. By employing such spot welding, as opposed to complete lamination of the stent-graft, it is possible to achieve stent-grafts having enhanced flexibility.

The above-described lamination method using dies can be used alone or in conjunction with other bonding methods. For example, such a method can be used in conjunction with adhesion if additional reinforcement is desired.

Various other modifications to the foregoing disclosed embodiments will now be evident to those skilled in the art. Thus, the particularly described embodiments are intended to be illustrative and not limiting. The true scope of the invention is set forth in the following claims.

What is claimed is:

1. A graft comprising:
   (i) a trunk;
   (ii) at least one first branch comprising a first member; and
   (iii) at least one second branch comprising a second member;
   wherein said first branch and said second branch define at least one crotch area, wherein at least a portion of said first member overlaps with at least a portion of said second member to form an overlapping section, and wherein at least one of said members comprises a continuous, uninterrupted section of PTFE which spans at least a portion of said crotch area.

2. The graft of claim 1, wherein said PTFE comprises ePTFE.

3. The graft of claim 1, wherein said PTFE is unsintered, partially sintered or completely sintered.

4. The graft of claim 1, wherein said graft further comprises at least one other member comprising PTFE.

5. The graft of claim 4, wherein said at least one other member comprises at least one flap.

6. The graft of claim 5, wherein said flap covers said crotch area of said graft.

7. The graft of claim 4, wherein said at least one other member comprises at least one strip.

8. The graft of claim 7, wherein said strip covers said crotch area of said graft.

9. The graft of claim 1, wherein said overlapping section spans at least a portion of said crotch area.

10. The graft of claim 9, wherein said overlapping section comprises a continuous, uninterrupted section of PTFE.

11. The graft of claim 1, wherein at least one of said members is tubular or substantially tubular.

12. The graft of claim 1, wherein at least one of said members has a non-uniform shape.

13. The graft of claim 1, wherein at least one of said members is formed from a tubular member comprising ePTFE or from a sheet comprising ePTFE.

14. The graft of claim 1, wherein at least one of said members has at least a first diameter and at least a second diameter, and wherein said second diameter is different than said first diameter.

15. A graft comprising:
   (i) a front side and a back side;
   (ii) at least two branches defining a crotch area;
   (iii) at least one sheet of ePTFE which wraps around the graft and comprises a continuous, uninterrupted section of ePTFE which spans the crotch area on the front side of the graft; and
   (iv) at least one sheet of ePTFE which wraps around the graft and comprises a continuous, uninterrupted section of ePTFE which spans the crotch area on the back side of the graft.

16. The graft of claim 15, wherein the crotch area comprises a bifurcation point.

17. A graft comprising:
   (i) a trunk;
   (ii) a crotch area; and (iii) at least one tubular member having a substantially flared end; wherein said tubular member comprises a continuous, uninterrupted section of ePTFE which spans said crotch area.

18. A graft comprising:
(i) an inner layer comprising at least one tubular member comprising a radially expanded portion and at least one branch portion;
(ii) an outer layer comprising at least one tubular member comprising a radially expanded portion and at least one branch portion;
wherein said radially expanded portion of said outer layer surrounds said radially expanded portion of said inner layer.

19. The graft of claim 18, wherein said graft comprises a crotch area.

20. The graft of claim 19, wherein at least one of said layer comprises continuous, uninterrupted eTPFE which spans the crotch area.

* * * * *